United States Patent
Scheerer

(10) Patent No.: US 8,796,454 B2
(45) Date of Patent: Aug. 5, 2014

(54) SYNTHESIS OF [2.2.2]-DIAZABICYCLIC RING SYSTEMS

(71) Applicant: College of William and Mary, Williamsburg, VA (US)

(72) Inventor: Jonathan R. Scheerer, Williamsburg, VA (US)

(73) Assignee: College of William and Mary, Williamsburg, VA (US)

( * ) Notice: Subject to any disclaimer, the term of this patent is extended or adjusted under 35 U.S.C. 154(b) by 0 days.

(21) Appl. No.: 13/874,829

(22) Filed: May 1, 2013

(65) Prior Publication Data

US 2013/0296564 A1  Nov. 7, 2013

Related U.S. Application Data

(60) Provisional application No. 61/642,536, filed on May 4, 2012.

(51) Int. Cl.

| | | |
|---|---|---|
| *C07D 487/08* | (2006.01) | |
| *C07D 498/08* | (2006.01) | |
| *C07D 487/18* | (2006.01) | |
| *C07D 498/18* | (2006.01) | |
| *C07D 471/20* | (2006.01) | |
| *C07D 471/08* | (2006.01) | |
| *C07D 498/22* | (2006.01) | |

(52) U.S. Cl.
CPC ............ *C07D 498/08* (2013.01); *C07D 487/18* (2013.01); *C07D 498/18* (2013.01); *C07D 471/20* (2013.01); *C07D 487/08* (2013.01); *C07D 471/08* (2013.01); *C07D 498/22* (2013.01)
USPC .......................................................... 544/349

(58) Field of Classification Search
CPC ................................................... C07D 487/08
See application file for complete search history.

(56) References Cited

PUBLICATIONS

Jin, S., et al. "Intermolecular and Intramolecular Diels-Alder Cycloadditions of 3-Ylidenepiperazine-2,5-diones and 5-Acyloxy-2(1H)-pyrazinones." J. Org. Chem. (2001), vol. 66, pp. 3984-3997.*
"Reagent Friday: Potassium t-butoxide." © Oct. 2011. Available from: <http://web.archive.org/web/20111031180452/http://masterorganicchemistry.com/2011/10/29/reagent-friday-kotbu/ >.*
Sheldon, R.A. "E factors, green chemistry, and catalysis: an odyssey." Chem. Comm. (2008), pp. 3352-3365.*
Margrey, K., et al. "Efficient Entry to the [2.2.2]-Diazabicyclic Ring System via Diastereoselective Domino Reaction Sequence." Organic Letters. (2012), vol. 14, No. 10, pp. 2458-2461.*
Williams, R.M. "Total Synthesis and Biosynthesis of the Paraherquamides: An Intriguing Story of the Biological Diels-Alder Construction", Chem. Pharm. Bull. (2002), vol. 50(6), p. 711-740.
Williams et al., "Paraherquamides, Brevianamides, and Asperparalines: Laboratory Synthesis and Biosynthesis. An Interim Report", Acc. Chem. Res. (2003), vol. 36, p. 127-139.
Greshock et al., "Improved Biomimetic Total Synthesis of D,L-Stephacidin A", Org. Lett. (2007), vol. 9, p. 4255-4258.
Miller et al., "Synthetic approaches to the bicyclo[2.2.2]diazaoctane ring system common to the paraherquamides, stephacidins and related prenylated indole alkaloids", Chem. Soc. Rev. (2009), vol. 38, p. 3160-3174.

* cited by examiner

*Primary Examiner* — Noble Jarrell
*Assistant Examiner* — John S Kenyon
(74) *Attorney, Agent, or Firm* — Jason P. McDevitt

(57) ABSTRACT

Herein we describe compositions and methods for the synthesis of [2.2.2]-diazabicyclic structures comprising a domino reaction sequence involving aldol condensation, alkene isomerization, and intramolecular hetero-Diels-Alder cycloaddition. Excellent diastereofacial control during the cycloaddition is enforced with a removable chiral phenyl aminal diketopiperazine substituent. The reaction sequence rapidly generates molecular complexity and is competent with both enolizable and non-enolizable aldehyde substrates. This method provides an efficient route to [2.2.2]-diazabicyclic structures, common to bioactive prenylated indole alkaloids such as the brevianamides and stephacidins.

9 Claims, 4 Drawing Sheets

SYNTHESIS OF [2.2.2]-DIAZABICYCLIC RING SYSTEMS

CROSS-REFERENCE TO RELATED APPLICATIONS

This patent application claims the benefit of and priority to U.S. Provisional Patent Application Ser. No. 61/642,536, filed May 4, 2012, the entire contents of which are herein incorporated by reference.

STATEMENT REGARDING FEDERALLY SPONSORED RESEARCH OR DEVELOPMENT

Not applicable

FIELD OF INVENTION

The present invention relates to the synthesis of [2.2.2]-diazabicyclic structures via a novel domino reaction sequence.

BACKGROUND

The [2.2.2]-diazabicyclic ring skeleton is shared among a number of prenylated indole alkaloids including the brevianamides, paraherquamides, stephacidins, notamides, and malbrancheamides (see FIG. 1, and see also Williams, R. M. *Chem. Pharm. Bull.*, 2002, 50, 711-740; Williams, R. M.; Cox, R. J. *Acc. Chem. Res.* 2003, 36 (2), 127-139). These fungal-derived natural products possess a wide spectrum of biological activities including antitumor, antihelmintic, antibacterial, calmodulin inhibition, and insecticidal properties, see Qian-Cutrone, J. F.; Huang, S.; Shu, Y. Z.; Vyas, D.; Fairchild, C.; Menendez, A.; Krampitz, K.; Dalterio, R.; Klohr, S. E.; Gao, Q., *J. Am. Chem. Soc* 2002, 124, 14556-14557; Martinez-Luis, S.; Rodriguez, R.; Acevedo, L.; Gonzalez, M. C.; Lira-Rocha, A.; Mata, R., *Tetrahedron* 2006, 62 (8), 1817-1822; Williams, R. M.; Stocking, E. M.; Sanz-Cervera, J. F., *Top. Curr. Chem.,* 2000, 209, 97-173. Impressive structural diversity is observed across the alkaloid family, although all members share a [2.2.2]-diazabicyclic core.

In addition to potent bioactivity and remarkable chemical structure, there are engaging biosynthetic questions regarding the origin of the [2.2.2]-diazabicyclic structural motif. The functionality is putatively derived from a biogenic intramolecular hetero-Diels-Alder cycloaddition (Williams, R. M.; Stocking, E. M.; Sanz-Cervera, J. F., Biosynthesis of prenylated alkaloids derived from tryptophan. In *Biosynthesis: Aromatic Polyketides, Isoprenoids, Alkaloids*, Springer-Verlag Berlin: Berlin, 2000; Vol. 209, pp 97-173). Alkaloids within this family have attracted significant attention from the synthetic community. In the context of total synthesis, five general synthetic strategies have been successfully employed to prepare the [2.2.2]-diazabicyclic core (see review of synthetic approaches from Miller, K. A.; Williams, R. M. *Chem. Soc. Rev.* 2009, 38, 3160-3174): (1) biomimetic Diels-Alder cycloaddition (Williams, R. M. *Chem. Pharm. Bull.* 2002, 50, 711-740; Williams, R. M.; Cox, R. J. *Acc. Chem. Res.* 2003, 36, 127-139; Jin, S.; Wessig, P.; Liebscher. J. *J. Org. Chem.* 2001, 66, 3984-3997), (2) radical cyclization (Herzon, S. B.; Myers, A. G. *J. Am. Chem. Soc.* 2005, 127 (15), 5342-5344; Crick, P. J.; Simpkins, N. S.; Highton, A. *Org. Lett.* 2011, 13, 6472-6475; Simpkins, N.; Pavlakos, I.; Male, L. *Chem. Commun.* 2012, 48, 1958-1960), (3) oxidative enolate coupling (Baran, P. S.; Hafensteiner, B. D.; Ambhaikar, N. B.; Guerrero, C. A.; Gallagher, J. D., *J. Am. Chem. Soc.* 2006, 128, 8678-8693), (4) $S_N2'$ enolate alkylation (Williams, R. M.; Glinka, T.; Kwast, E. *J. Am. Chem. Soc.* 1988, 110, 5927-5929; Cushing, T. D.; Sanz-Cervera, J. F.; Williams, R. M. *J. Am. Chem. Soc.,* 1993, 115, 9323-9324; Artman, G. D.; Grubbs, A. W.; Williams, R. M. *J. Am. Chem. Soc.,* 2007, 129, 6336-6342) and (5) cation-olefin cyclization (Frebault, F. C.; Simpkins, N. S. *Tetrahedron* 2010, 66, 6585-6596; Frebault, F.; Simpkins, N. S.; Fenwick, A. *J. Am. Chem. Soc.* 2009, 131, 4214-4215).

The biomimetic Diels-Alder approach provides one of the most efficient entries to the [2.2.2]-diazabicyclic core. In the laboratory, the biomimetic Diels-Alder reaction often suffers from limited stereoselectivity. For example, in the key step of the elegant synthesis of stephacidin A (5) by Williams and co-workers (Greshock, T. J.; Williams, R. M. *Org. Lett.* 2007, 9, 4255-4258), prestephacidin reacts via intramolecular Diels-Alder cycloaddition to afford diastereomeric [2.2.2]-bicyclic products in a 2.1:1 diastereomeric ratio. This modest diastereomeric ratio has been consistent with other related biomimetic Diels-Alder cycloadditions.

There is a need in the art for an efficient, stereoselective entry to the [2.2.2]-diazabicyclic core.

BRIEF SUMMARY OF THE INVENTION

Herein we describe a process for preparing [2.2.2.]-diazabicyclic structures comprising reacting a diketopiperazine, an aldehyde, and a substituted unsaturated hydrocarbon under basic conditions to perform a three step reaction comprising sequentially an aldol condensation, an alkene isomerization, and a Diels-Alder cycloaddition to produce a [2.2.2.]-diazabicyclic structure.

Herein we also describe novel [2.2.2.]-diazabicyclic structures.

The process is experimentally simple and has tremendous scope, providing an efficient route to [2.2.2]-diazabicyclic structures, common to bioactive prenylated indole alkaloids such as the brevianamides and stephacidins. A wide variety of reaction substrates can be used successfully, and a variety of bases can be used to perform the reaction. The substituted unsaturated hydrocarbon can be either an alkene or an alkyne, and the aldehyde can be enolizable or non-enolizable. The aldehyde and substituted unsaturated hydrocarbon can be connected as part of the same molecule, or they can be separate molecules.

One aspect of the present invention relates to a one-pot, domino reaction sequence involving aldol condensation, alkene isomerization, and intramolecular hetero-Diels-Alder cycloaddition for the synthesis of [2.2.2]-diazabicyclic structures. Excellent diastereofacial control during the cycloaddition is enforced with a removable chiral phenyl aminal diketopiperazine substituent. The reaction sequence rapidly generates molecular complexity, and can be performed without workup or purification between the three steps of the sequential reaction.

In certain embodiments, with an alkene substrate, a method of the present invention is represented by Scheme 1:

Scheme 1

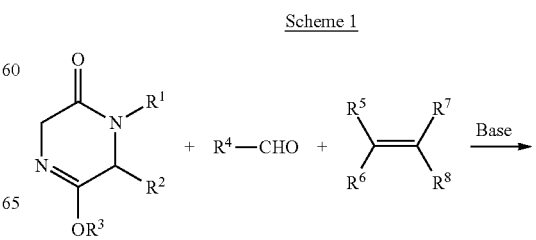

-continued

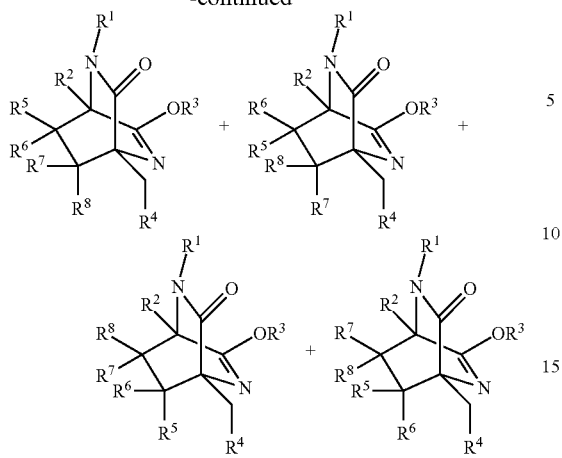

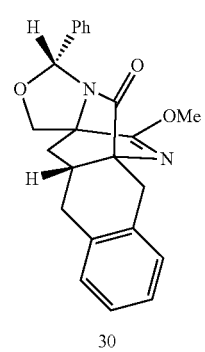

30

In certain embodiments, when the substituted unsaturated hydrocarbon is an alkyne substrate, a method of the present invention is represented by Scheme 2:

In certain embodiments, the methods of the present invention are represented by Scheme 1 and the attendant definitions, wherein $R^1$ represents hydrogen, alkyl, aryl, or substituted alkyl or substituted aryl, including aryl heterocycles; $R^2$ represents any permissible atom, including hydrogen, alkyl, or aryl, or substituted alkyl or substituted aryl; $R^3$ represents alkyl, aryl, substituted alkyl, or substituted aryl; and $R^4$, $R^5$, $R^6$, $R^7$ and $R^8$ represent hydrogen, alkyl, aryl, or substituted alkyl or substituted aryl, including aryl heterocycles. In some embodiments according to Scheme 1 above, $R^1$ and $R^2$ join together to form a ring.

In some embodiments, the aldehyde reactant and the alkene reactant are connected as a single reactant, i.e., an alkenal wherein $R^4$ is connected to either $R^5$ or $R^6$, in which case the products are limited to the following diastereomers:

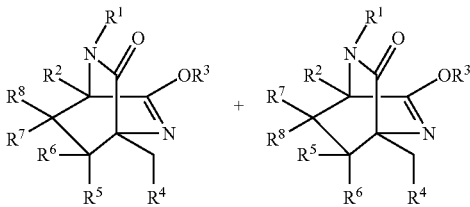

In some embodiments, the choice of base used to initiate the reaction depends on whether the aldehyde is enolizable. If the aldehyde is enolizable, then the enolate of the aldehyde is first prepared using, for example, a lithium amide base such as LiHDMS. If the aldehyde is not enolizable, then an alkoxide or phenoxide base such as sodium methoxide can be used to initiate the reaction, which is particularly attractive when reactions are performed on a large scale.

In one representative embodiment, the cycloadduct 30 was prepared from the diketopiperazine 10 and alkenal 1 by refluxing in sodium methoxide and methanol, yielding cycloadduct 30 in 76% yield and favorable diastereoselectivity (>95:5).

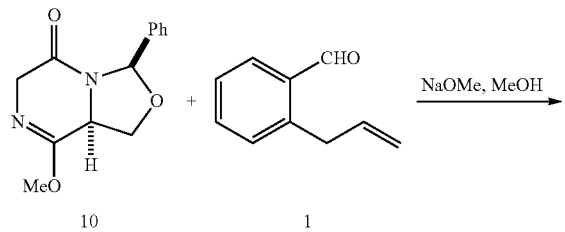

Scheme 2

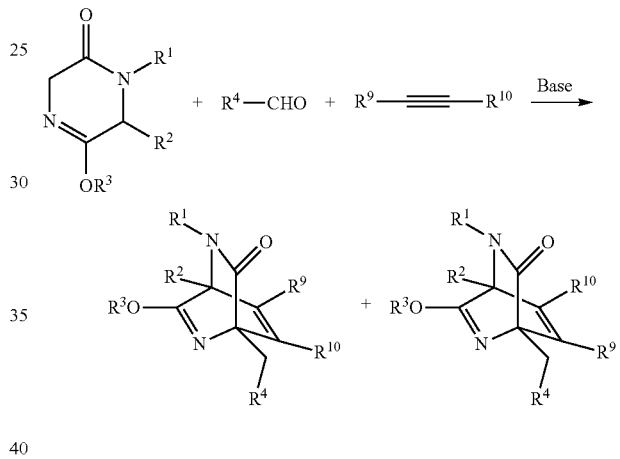

In certain embodiments, the methods of the present invention are represented by Scheme 2 and the attendant definitions, wherein $R^1$ represents hydrogen, alkyl, aryl, or substituted alkyl or substituted aryl, including aryl heterocycles; $R^2$ represents any permissible atom, including hydrogen, alkyl, or aryl, or substituted alkyl or substituted aryl; $R^3$ represents alkyl, aryl, substituted alkyl, or substituted aryl; and $R^4$, $R^9$, and $R^{10}$ represent hydrogen, alkyl, aryl, or substituted alkyl or substituted aryl, including aryl heterocycles.

For example, in one embodiment, the diketopiperazine 12 reacts with alkynal 20 to form the cycloadduct 40 in 54% yield.

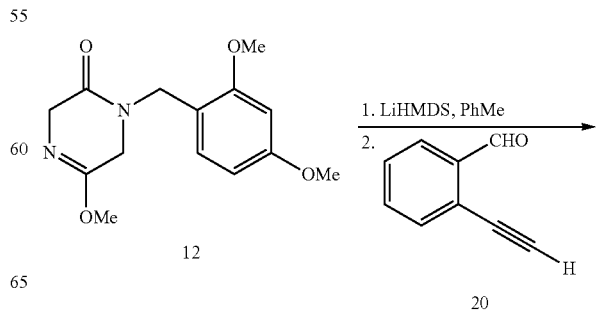

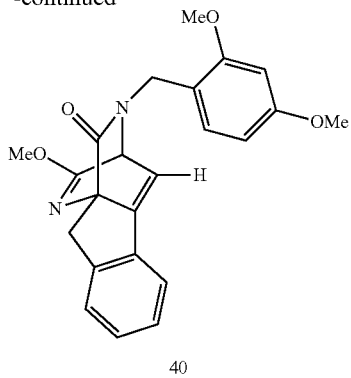

40

DETAILED DESCRIPTION OF THE INVENTION

Figure 1:
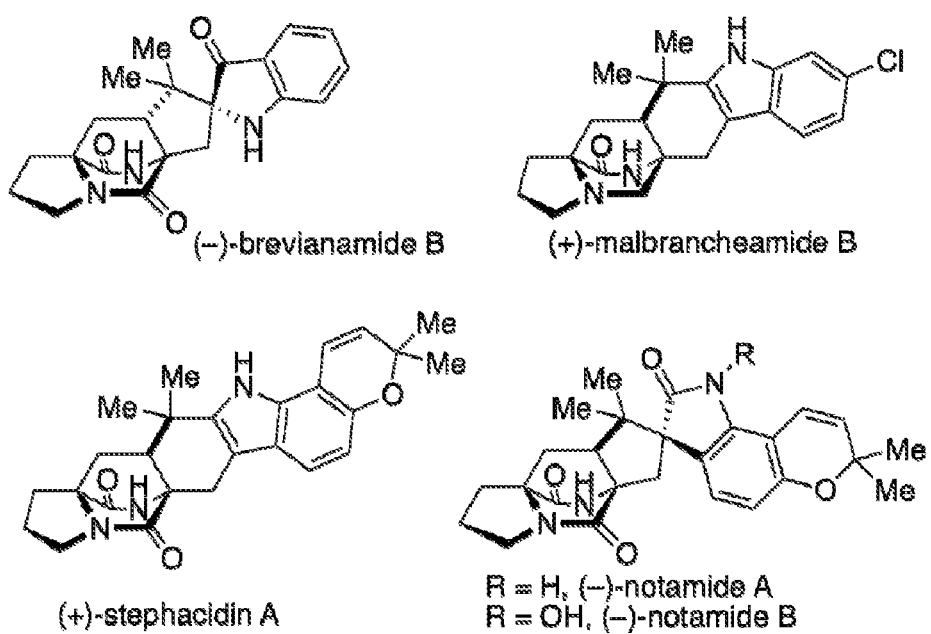
FIG. 1 depicts several well-known compounds having a [2.2.2]-diazabicyclic core.

Herein we describe a process for preparing [2.2.2.]-diazabicyclic structures comprising reacting a diketopiperazine, an aldehyde, and a substituted unsaturated hydrocarbon under basic conditions to perform a three step reaction comprising sequentially an aldol condensation, an alkene isomerization, and a Diels-Alder cycloaddition to form a [2.2.2.]-diazabicyclic structure.

The process provides an efficient route to [2.2.2]-diazabicyclic structures, common to bioactive prenylated indole alkaloids such as the brevianamides and stephacidins. A wide variety of reaction substrates can be used successfully, and a variety of bases can be used to perform the reaction. The substituted unsaturated hydrocarbon can be either an alkene or an alkyne, and the aldehyde can be enolizable or non-enolizable. The aldehyde and substituted unsaturated hydrocarbon can be connected as part of the same molecule, or they can be separate molecules.

Definitions

For convenience, certain terms employed in the specification, examples, and appended claims are collected here.

The term "nucleophile" is recognized in the art, and as used herein means a chemical moiety having a reactive pair of electrons. Examples of nucleophiles include uncharged compounds such as water, amines, mercaptans and alcohols, and charged moieties such as alkoxides, thiolates, carbanions, and a variety of organic and inorganic anions. Illustrative anionic nucleophiles include simple anions such as hydroxide, azide, cyanide, thiocyanate, acetate, formate or chloroformate, and bisulfite. Organometallic reagents such as organocuprates, organozincs, organolithiums, Grignard reagents, enolates, acetylides, and the like may, under appropriate reaction conditions, be suitable nucleophiles. Hydride may also be a suitable nucleophile when reduction of the substrate is desired.

The term "electrophile" is art-recognized and refers to chemical moieties which can accept a pair of electrons from a nucleophile as defined above. Electrophiles useful in the method of the present invention include cyclic compounds such as epoxides, aziridines, episulfides, cyclic sulfates, carbonates, lactones, lactams and the like. Non-cyclic electrophiles include sulfates, sulfonates (e.g. tosylates), chlorides, bromides, iodides, and the like.

The terms "electrophilic atom", "electrophilic center" and "reactive center" as used herein refer to the atom of the substrate which is attacked by, and forms a new bond to, the nucleophile. In most (but not all) cases, this will also be the atom from which the leaving group departs.

The term "electron-withdrawing group" is recognized in the art and as used herein means a functionality which draws electrons to itself more than a hydrogen atom would at the same position. Exemplary electron-withdrawing groups include nitro, ketone, aldehyde, sulfonyl, trifluoromethyl, —CN, chloride, and the like.

The term "electron-donating group", as used herein, means a functionality which draws electrons to itself less than a hydrogen atom would at the same position. Exemplary electron-donating groups include amino, methoxy, and the like.

The term "polar solvent" refers to a solvent with a dielectric constant greater than or equal to about 20. For example, water, methanol, dimethyl sulfoxide, N,N-dimethylformamide and acetonitrile are polar solvents.

The terms "Lewis base" and "Lewis basic" are recognized in the art, and refer to a chemical moiety capable of donating a pair of electrons under certain reaction conditions. Examples of Lewis basic moieties include uncharged compounds such as alcohols, thiols, olefins, and amines, and charged moieties such as alkoxides, thiolates, carbanions, and a variety of other organic anions.

The term "Bronsted base" is art-recognized and refers to an uncharged or charged atom or molecule, e.g., an oxide, amine, alkoxide, or carbonate that is a proton acceptor. The term "base" encompasses both Lewis bases and Bronsted bases.

The terms "Lewis acid" and "Lewis acidic" are art-recognized and refer to chemical moieties which can accept a pair of electrons from a Lewis base.

The term "meso compound" is recognized in the art and means a chemical compound which has at least two chiral centers but is achiral due to an internal plane, or point, of symmetry.

The term "chiral" refers to molecules which have the property of non-superimposability on their mirror image partner, while the term "achiral" refers to molecules which are superimposable on their mirror image partner. A "prochiral molecule" is an achiral molecule which has the potential to be converted to a chiral molecule in a particular process.

The term "stereoisomers" refers to compounds which have identical chemical constitution, but differ with regard to the arrangement of their atoms or groups in space. In particular, the term "enantiomers" refers to two stereoisomers of a compound which are non-superimposable mirror images of one another. The term "diastereomers", on the other hand, refers to the relationship between a pair of stereoisomers that comprise two or more asymmetric centers and are not mirror images of one another.

Furthermore, a "stereoselective process" is one which produces a particular stereoisomer of a reaction product in preference to other possible stereoisomers of that product. An "enantioselective process" is one which favors production of one of the two possible enantiomers of a reaction product. The subject method is said to produce a "stereoselectively-enriched" product (e.g., enantioselectively-enriched or diastereoselectively-enriched) when the yield of a particular stereoisomer of the product is greater by a statistically significant amount relative to the yield of that stereoisomer resulting from the same reaction run in the absence of a chiral catalyst. For example, an enantioselective reaction catalyzed by one of the subject chiral catalysts will yield an enantiomeric excess for a particular enantiomer that is larger than the enantiomeric excess of the reaction lacking the chiral catalyst.

The term "regioisomers" refers to compounds which have the same molecular formula but differ in the connectivity of the atoms. Accordingly, a "regioselective process" is one which favors the production of a particular regioisomer over others, e.g., the reaction produces a statistically significant preponderance of a certain regioisomer.

The term "reaction product" means a compound which results from the reaction of a nucleophile and a substrate. In general, the term "reaction product" will be used herein to refer to a stable, isolable compound, and not to unstable intermediates or transition states.

The term "catalytic amount" is recognized in the art and means a substoichiometric amount relative to a reactant.

As discussed more fully below, the reactions contemplated in the present invention include reactions which are enantioselective, diastereoselective, and/or regioselective. An enantioselective reaction is a reaction which converts an achiral reactant to a chiral product enriched in one enantiomer. Enantioselectivity is generally quantified as "enantiomeric excess" (ee) defined as follows:

% Enantiomeric Excess $A$ (ee)=(% Enantiomer $A$)−(% Enantiomer $B$)

where A and B are the enantiomers formed. Additional terms that are used in conjunction with enatioselectivity include "optical purity" or "optical activity". An enantioselective reaction yields a product with an ee greater than zero. Preferred enantioselective reactions yield a product with an ee greater than 20%, more preferably greater than 50%, even more preferably greater than 70%, and most preferably greater than 80%.

A diastereoselective reaction converts a chiral reactant (which may be racemic or enantiomerically pure) to a product enriched in one diastereomer. If the chiral reactant is racemic, in the presence of a chiral non-racemic reagent or catalyst, one reactant enantiomer may react more slowly than the other. This class of reaction is termed a kinetic resolution, wherein the reactant enantiomers are resolved by differential reaction rate to yield both enantiomerically-enriched product and enantimerically-enriched unreacted substrate. Kinetic resolution is usually achieved by the use of sufficient reagent to react with only one reactant enantiomer (i.e. one-half mole of reagent per mole of racemic substrate). Examples of catalytic reactions which have been used for kinetic resolution of racemic reactants include the Sharpless epoxidation and the Noyori hydrogenation.

A regioselective reaction is a reaction which occurs preferentially at one reactive center rather than another non-identical reactive center. For example, a regioselective reaction of an unsymmetrically substituted epoxide substrate would involve preferential reaction at one of the two epoxide ring carbons.

The term "non-racemic" with respect to the chiral catalyst, means a preparation of catalyst having greater than 50% of a given enantiomer, more preferably at least 75%. "Substantially non-racemic" refers to preparations of the catalyst which have greater than 90% ee for a given enantiomer of the catalyst, more preferably greater than 95% ee.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$-$C_{30}$ for straight chain, $C_3$-$C_{30}$ for branched chain), and more preferably 20 of fewer. Likewise, preferred cycloalkyls have from 4-10 carbon atoms in their ring structure, and more preferably have 5, 6 or 7 carbons in the ring structure.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths.

The term "substituted unsaturated hydrocarbon" refers to alkenes and alkynes, either entirely hydrocarbons or optionally substituted with any other functional groups.

The terms "alkenyl" and "alkynyl" refer to unsaturated aliphatic groups analogous in length and possible substitution to the alkyls described above, but which contain at least one double or triple carbon-carbon bond, respectively.

The term "organometallic" refers to compounds comprising a metallic atom (such as mercury, zinc, lead, magnesium or lithium) or a metalloid atom (such as silicon, or tin) that is bonded directly to a carbon atom, such as methyl magnesium bromide, phenyl lithium, and phenyl-trimethyl-tin.

The terms "amine" and "amino" are art-recognized and refer to both unsubstituted and substituted amines, e.g., a moiety that can be represented by the general formula:

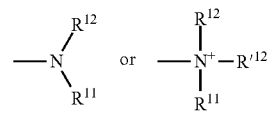

wherein $R^{11}$, $R^{12}$ and $R'^{12}$ each independently represent a group permitted by the rules of valence.

The term "acylamino" is art-recognized and refers to a moiety that can be represented by the general formula:

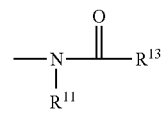

wherein $R^{11}$ is as defined above, and $R^{13}$ represents a hydrogen, an alkyl, an alkenyl or —$(CH_2)_m$—$R^{14}$, wherein m is zero or an integer in the range of 1 to 8, and $R^{14}$ represents an aryl, a cycloalkyl, a cycloalkenyl, a heterocycle, or a polycycle.

The term "amido" is art recognized as an amino-substituted carbonyl and includes a moiety that can be represented by the general formula:

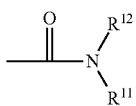

wherein $R^{11}$ and $R^{12}$ are as defined above.

The term "carbonyl" is art recognized and includes such moieties as can be represented by the general formula:

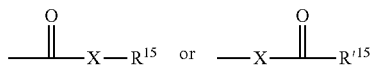

wherein X is a carbon bond or represents an oxygen or a sulfur, $R^{15}$ represents a hydrogen, an alkyl, an alkenyl, —$(CH_2)_m$—$R^{14}$ or a pharmaceutically acceptable salt, where m and $R^{14}$ are as defined above, and $R'^{15}$ represents a hydrogen, an alkyl, an alkenyl, or —$(CH_2)_m$—$R^{14}$, where m and $R^{14}$ are as defined above. Where X is an oxygen and $R^{15}$ or $R'^{15}$ is not hydrogen, the formula represents an "ester". Where X is an oxygen, and $R^{15}$ is as defined above, the moiety is referred to herein as a carboxyl group, and particularly when $R^{15}$ is a hydrogen, the formula represents a "carboxylic acid". Where X is an oxygen, and $R'^{15}$ is hydrogen, the formula represents a "formate". In general, where the oxygen atom of the above formula is replaced by sulfur, the formula represents a "thiolcarbonyl" group. Where X is a sulfur and $R^{15}$ or $R'^{15}$ is not hydrogen, the formula represents a "thiolester." Where X is a sulfur and $R^{15}$ is hydrogen, the formula represents a "thiolcarboxylic acid." Where X is a sulfur and $R'^{15}$ is hydrogen, the formula represents a "thiolformate." Where X is a carbon bond, and $R^{15}$ is not hydrogen, the above formula represents a "ketone" group. Where X is a carbon bond, and $R^{15}$ is hydrogen, the above formula represents an "aldehyde" group.

The term "alkynal" refers to a compound having both an alkyne group and an aldehyde group. The term "alkenal" refers to a compound having both an alkene group and an aldehyde group.

The terms "alkoxyl" or "alkoxy" as used herein refers to an alkyl group, as defined above, having an oxygen attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—$(CH2)m$-$R^{14}$, where m and $R^{14}$ are described above. The term "alkoxide" refers to an alkyl group having an anionic oxygen attached thereto; for example, sodium methoxide. The term "phenoxide" refers to any of a class of salts having a phenolate or substituted phenolate anion; e.g., sodium phenoxide.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the Journal of Organic Chemistry; this list is typically presented in a table entitled Standard List of Abbreviations. The abbreviations contained in said list, and all abbreviations utilized by organic chemists of ordinary skill in the art are hereby incorporated by reference.

Analogous substitutions can be made to alkenyl and alkynyl groups to produce, for example, alkenylamines, alkynylamines, alkenylamides, alkynylamides, alkenylimines, alkynylimines, thioalkenyls, thioalkynyls, carbonyl-substituted alkenyls or alkynyls, alkenoxyls, alkynoxyls, metalloalkenyls and metalloalkynyls, all of which are substituted unsaturated hydrocarbons.

The term "aryl" as used herein includes 4-, 5-, 6- and 7-membered single-ring aromatic groups which may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycle". The aromatic ring can be substituted at one or more ring positions with such substituents as described above, as for example, halogens, alkyls, alkenyls, alkynyls, hydroxyl, amino, nitro, thiol amines, imines, amides, phosphonates, phosphines, carbonyls, carboxyls, silyls, ethers, thioethers, sulfonyls, selenoethers, ketones, aldehydes, esters, or —$(CH_2)_m$—$R^{14}$, —$CF_3$, —CN, or the like, where m and $R^{14}$ are described above.

The terms "heterocycle" or "heterocyclic group" refer to 4 to 10-membered ring structures, more preferably 5 to 7 membered rings, which ring structures include one to four heteroatoms. Heterocyclic groups include pyrrolidine, oxolane, thiolane, imidazole, oxazole, piperidine, piperazine, morpholine. The heterocyclic ring can be substituted at one or more positions with such substituents as described above, as for example, halogens, alkyls, alkenyls, allynyls, hydroxyl, amino, nitro, thiol, amines, imines, amides, phosphonates, phosphines, carbonyls, carboxyls, silyls, ethers, thioethers, sulfonyls, selenoethers, ketones, aldehydes, esters, or —$(CH_2)_m$—$R_{14}$, —$CF_3$, —CN, or the like, where m and $R^{14}$ are described above.

The terms "polycycle" or "polycyclic group" refer to two or more cyclic rings (e.g., cycloalkyls, cycloalkenyls, cycloalkynyls, aryls and/or heterocycles) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogens, alkyls, alkenyls, alkynyls, hydroxyl, amino, nitro, thiol, amines, imines, amides, phosphonates, phosphines, carbonyls, carboxyls, silyls, ethers, thioethers, sulfonyls, selenoethers, ketones, aldehydes, esters, or —$(CH_2)_m$—$R_{14}$, —$CF_3$, —CN, or the like, where m and $R^{14}$ are described above.

The term "heteroatom" as used herein means an atom of any element other than carbon or hydrogen. Preferred heteroatoms are nitrogen, oxygen, sulfur, phosphorus and selenium.

For purposes of this invention, the chemical elements are identified in accordance with the Periodic Table of the Elements, CAS version, Handbook of Chemistry and Physics, 67th Ed., 1986-87, inside cover.

The terms ortho, meta and para apply to 1,2-, 1,3- and 1,4-disubstituted benzenes, respectively. For example, the names 1,2-dimethylbenzene and ortho-dimethylbenzene are synonymous.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described hereinabove. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. This invention is not intended to be limited in any manner by the permissible substituents of organic compounds.

The terms "aldol condensation", "alkene isomerization", and "Diels-Alder cycloaddition" refer to reaction types well-known in the art.

The term "purification and isolation of the products" refers to conventional methods for isolating and purifying products of a chemical reaction, and for the purposes herein, means taking steps to isolate and purify reaction products to a purity of at least 90% by weight.

Combinatorial Libraries—The subject reactions readily lend themselves to the creation of combinatorial libraries of compounds for the screening of pharmaceutical, agrochemical or other biological or medically-related activity or material-related qualities. A combinatorial library for the purposes of the present invention is a mixture of chemically related compounds which may be screened together for a desired property; said libraries may be in solution or covalently linked to a solid support. The preparation of many related compounds in a single reaction greatly reduces and simplifies the number of screening processes which need to be carried out. Screening for the appropriate biological, pharmaceutical, agrochemical or physical property may be done by conventional methods.

Given the need in the art for an efficient, stereoselective synthetic process to produce compounds having a [2.2.2]-diazabicyclic core, we pursued an approach based on a chiral diketopiperazine (DKP) azadiene in order to control facial selectivity of the reaction. This approach is shown in Scheme 1 and Scheme 2, which entail a domino reaction sequence involving aldol condensation, alkene isomerization, and intramolecular hetero-Diels-Alder cycloaddition (also referred to as "IMDA [4+2]") for the synthesis of [2.2.2]-diazabicyclic structures.

In certain embodiments, the methods of the present invention are represented by Scheme 1 and the attendant definitions, wherein $R^1$ represents hydrogen, alkyl, aryl, or substituted alkyl or substituted aryl, including aryl heterocycles; $R^2$ represents any permissible atom, including hydrogen, alkyl, or aryl, or substituted alkyl or substituted aryl; $R^3$ represents alkyl, aryl, substituted alkyl, or substituted aryl; and $R^4$, $R^5$, $R^6$, $R^7$ and $R^8$ represent hydrogen, alkyl, aryl, or substituted alkyl or substituted aryl, including aryl heterocycles.

In certain embodiments, the methods of the present invention are represented by Scheme 1 and the attendant definitions, wherein $R^1$ represents hydrogen, alkyl, aryl, or substituted alkyl or substituted aryl, including aryl heterocycles; $R^2$ represents any permissible atom, including hydrogen, alkyl, or aryl, or substituted alkyl or substituted aryl; $R^3$ represents alkyl, aryl, substituted alkyl, or substituted aryl; and $R^4$, $R^5$, $R^6$, $R^7$ and $R^8$ represent hydrogen, alkyl, aryl, or substituted alkyl or substituted aryl, including aryl heterocycles, and wherein $R^1$ and $R^2$ are joined together to form a 5-membered ring, which in some embodiments contains a heteroatom.

In certain embodiments, the methods of the present invention are represented by Scheme 1 and the attendant definitions, wherein $R^1$ represents hydrogen, alkyl, aryl, or substituted alkyl or substituted aryl, including aryl heterocycles; $R^2$ represents any permissible atom, including hydrogen, alkyl, or aryl, or substituted alkyl or substituted aryl; $R^3$ represents alkyl, aryl, substituted alkyl, or substituted aryl; and $R^4$, $R^5$, $R^6$, $R^7$ and $R^8$ represent hydrogen, alkyl, aryl, or substituted alkyl or substituted aryl, including aryl heterocycles; and wherein the aldehyde substrate and alkene substrate are linked together intramolecularly, e.g., when $R^4$ and $R^5$ are linked. For example, allyl benzaldehyde contains both an aldehyde and an alkene, and combines with DKP 10 to produce cycloadduct 30 along with a small fraction of its diastereomer. In some embodiments, $R^4$ and $R^5$ are linked such that $R^4$ and $R^5$ comprise a chain having between 2 and 5 atoms in the main chain, wherein said main chain atoms can be carbon or in some embodiments can include one or more heteroatoms including oxygen and/or nitrogen.

In certain embodiments, suitable diketopiperazine starting materials include, but are not limited to: Pyrrolo[1,2-a]pyrazin-4(3H)-one, 6,7,8,8a-tetrahydro-1-methoxy-, (8aS)- (CAS Registry Number 916504-58-0); 3H-Oxazolo[3,4-a]pyrazin-5(1H)-one, 3-(1,1-dimethylethyl)-6,8a-dihydro-8-methoxy-, (3R,8aS)-(CAS Registry Number 1315536-92-5); Pyrrolo[1,2-a]pyrazin-4(3H)-one, 1-ethoxy-6,7,8,8a-tetrahydro-, (S)-(9Cl) (CAS Registry Number 49652-00-8); 3H-Oxazolo[3,4-a]pyrazin-5(6H)-one, 3-(1,1-dimethylethyl)-8-methoxy-, (3R)-(CAS Registry Number 1315536-96-9); [1,3]Azasilolo[1,5-a]pyrazin-5(1H)-one, 8-ethoxy-2,3,6,8a-tetrahydro-2,2-dimethyl (CAS Registry Number 325966-75-4); 2(1H)-Pyrazinone, 3,6-dihydro-5-methoxy-1-methyl-(CAS Registry Number 179686-28-3); 4H-Pyrazino[1,2-b]isoquinolin-4-one, 3,6,11,11a-tetrahydro-1-methoxy-, (11aS)-(CAS Registry Number 508209-89-0); and 2(1H)-Pyrazinone, 5-ethoxy-3,6-dihydro-1-methyl-(CAS Registry Number 54799-47-2).

In certain embodiments, the methods of the present invention are represented by Scheme 2 and the attendant definitions, wherein $R^1$ represents hydrogen, alkyl, aryl, or substituted alkyl or substituted aryl, including aryl heterocycles; $R^2$ represents any permissible atom, including hydrogen, alkyl, or aryl, or substituted alkyl or substituted aryl; $R^3$ represents alkyl, aryl, substituted alkyl, or substituted aryl; and $R^4$, $R^9$ and $R^{10}$ represent hydrogen, alkyl, aryl, or substituted alkyl or substituted aryl, including aryl heterocycles.

In certain embodiments, the methods of the present invention are represented by Scheme 2 and the attendant definitions, wherein $R^1$ represents hydrogen, alkyl, aryl, or substituted alkyl or substituted aryl, including aryl heterocycles; $R^2$ represents any permissible atom, including hydrogen, alkyl, or aryl, or substituted alkyl or substituted aryl; $R^3$ represents alkyl, aryl, substituted alkyl, or substituted aryl; and $R^4$, $R^9$ and $R^{10}$ represent hydrogen, alkyl, aryl, or substituted alkyl or substituted aryl, including aryl heterocycles, and wherein $R^1$ and $R^2$ are joined together to form a 5-membered ring, which in some embodiments contains a heteroatom.

In certain embodiments, the methods of the present invention are represented by Scheme 1 and the attendant definitions, wherein $R^1$ represents hydrogen, alkyl, aryl, or substituted alkyl or substituted aryl, including aryl heterocycles; $R^2$ represents any permissible atom, including hydrogen, alkyl, or aryl, or substituted alkyl or substituted aryl; $R^3$ represents alkyl, aryl, substituted alkyl, or substituted aryl; and $R^4$, $R^9$, and $R^{10}$ represent hydrogen, alkyl, aryl, or substituted alkyl or substituted aryl, including aryl heterocycles; and wherein the aldehyde substrate and alkyne substrate are linked together intramolecularly, e.g., when $R^4$ and $R^9$ are linked. For example, the alkynal 20 contains both an aldehyde and an alkyne, and combines with DKP 12 to produce cycloadduct 40. In some embodiments, $R^4$ and $R^9$ are linked such that $R^4$ and $R^9$ comprise a chain having between 2 and 5 atoms in the main chain, wherein said main chain atoms can be carbon or in some embodiments can include one or more heteroatoms including oxygen and/or nitrogen.

In certain embodiments, suitable diketopiperazine starting materials include, but are not limited to: Pyrrolo[1,2-a]pyrazin-4(3H)-one, 6,7,8,8a-tetrahydro-1-methoxy-, (8aS)-(CAS Registry Number 916504-58-0); 3H-Oxazolo[3,4-a]pyrazin-5(1H)-one, 3-(1,1-dimethylethyl)-6,8a-dihydro-8-methoxy-, (3R,8aS)-(CAS Registry Number 1315536-92-5); Pyrrolo[1,2-a]pyrazin-4(3H)-one, 1-ethoxy-6,7,8,8a-tetrahydro-, (S)-(9Cl) (CAS Registry Number 49652-00-8); 3H-Oxazolo[3,4-a]pyrazin-5(6H)-one, 3-(1,1-dimethylethyl)-8-methoxy-, (3R)-(CAS Registry Number 1315536-96-9); [1,3]Azasilolo[1,5-a]pyrazin-5(1H)-one, 8-ethoxy-2,3,6,8a-tetrahydro-2,2-dimethyl (CAS Registry Number 325966-75-4); 2(1H)-Pyrazinone, 3,6-dihydro-5-methoxy-1-methyl-(CAS Registry Number 179686-28-3); 4H-Pyrazino[1,2-b]isoquinolin-4-one, 3,6,11,11a-tetrahydro-1-methoxy-, (11aS)-(CAS Registry Number 508209-89-0); and 2(1H)-Pyrazinone, 5-ethoxy-3,6-dihydro-1-methyl-(CAS Registry Number 54799-47-2).

Reaction Conditions

The reactions of the present invention may be performed under a wide range of conditions, though it will be understood that the solvents and temperature ranges recited herein are not limitative and only correspond to a preferred mode of the process of the invention.

Representative embodiments of the process have typically been carried out under General Conditions A or General Conditions B described below, but many other reaction conditions will be sufficient in order to initiate and complete the three-step reaction sequence described herein.

In general, it will be desirable that reactions are run using mild conditions which will not adversely affect the reactants, the catalyst, or the product. For example, the reaction temperature influences the speed of the reaction, as well as the stability of the reactants, products and catalyst.

In general, the subject reactions are carried out in a liquid reaction medium. The reactions may be run without addition of solvent. Alternatively, the reactions may be run in an inert solvent, preferably one in which the reaction ingredients, including the catalyst, are substantially soluble. Suitable solvents include ethers such as diethyl ether, 1,2-dimethoxyethane, diglyme, t-butyl methyl ether, tetrahydrofuran and the like; alcohols such as ethanol and methanol and the like; halogenated solvents such as chloroform, dichloromethane, dichloroethane, chlorobenzene, and the like; aliphatic or aromatic hydrocarbon solvents such as benzene, xylene, toluene, hexane, pentane and the like; esters and ketones such as ethyl acetate, acetone, and 2-butanone; polar aprotic solvents such as acetonitrile, dimethylsulfoxide, dimethylformamide and the like; or combinations of two or more solvents.

The invention also contemplates reaction in a biphasic mixture of solvents, in an emulsion or suspension, or reaction in a lipid vesicle or bilayer. In certain embodiments, it may be preferred to perform the catalyzed reactions in the solid phase with one of the reactants anchored to a solid support.

In certain embodiments it is preferable to perform the reactions under an inert atmosphere of a gas such as nitrogen or argon.

The requisite base can be selected from the group consisting of hydrides, carbonates, alkoxides, phenoxides, amides, carbanions, and silyl anions. For reasons of, for example, cost and simplicity, it may be preferable to use alkoxides or phenoxides as the base when the aldehyde substrate is non-enolizable. In other cases, for example with alkynal reactants, alkoxides can cause degradation of the substrate, and thus other bases are preferred. Note that more than one base can be used during the reaction.

The reaction processes of the present invention can be conducted in continuous, semi-continuous or batch fashion and may involve a liquid recycle operation as desired. The processes of this invention are preferably conducted in batch fashion.

The reaction can be conducted in a single reaction zone or in a plurality of reaction zones, in series or in parallel or it may be conducted batchwise or continuously in an elongated tubular zone or series of such zones. The materials of construction employed should be inert to the starting materials during the reaction and the fabrication of the equipment should be able to withstand the reaction temperatures and pressures. Means to introduce and/or adjust the quantity of starting materials or ingredients introduced batchwise or continuously into the reaction zone during the course of the reaction can be conveniently utilized in the processes especially to maintain the desired molar ratio of the starting materials. The reaction steps may be affected by the incremental addition of one of the starting materials to the other. Also, the reaction steps can be combined by the joint addition of the starting materials to the metal catalyst. When complete conversion is not desired or not obtainable, the starting materials can be separated from the product and then recycled back into the reaction zone.

The processes may be conducted in either glass-lined, stainless steel or similar type reaction equipment. The reaction zone may be fitted with one or more internal and/or external heat exchanger(s) in order to control undue temperature fluctuations, or to prevent any possible "runaway" reaction temperatures.

Furthermore, one or more of the reactants can be immobilized or incorporated into a polymer or other insoluble matrix.

Subsequent Transformations. A product synthesized by a method of the present invention may be either an end-product or an intermediate in a synthesis scheme. In cases where the product synthesized by a method of the present invention is an intermediate, the product may be subjected to one or more additional transformations to yield the desired end-product. The set of additional transformations contemplated comprises isomerizations, hydrolyses, oxidations, reductions, additions, eliminations, olefinations, functional group interconversions, transition metal-mediated reactions, transition metal-catalyzed reactions, bond-forming reactions, cleavage reactions, fragmentation reactions, thermal reactions, photochemical reactions, cycloadditions, sigmatropic rearrangements, electrocyclic reactions, chemoselective reactions, regioselective reactions, stereoselective reactions, diastereoselective reactions, enantioselective reactions, and kinetic resolutions. The invention expressly comprises use of a method of the present invention as a step—either initial, intermediate or final—in the synthesis of known or new pharmaceuticals, e.g., antivirals, antibiotics, and analgesics.

EXAMPLES

The examples that follow are intended in no way to limit the scope of this invention but are provided to illustrate the methods of the present invention. Many other embodiments of this invention will be apparent to one skilled in the art.

General Conditions A for aldol condensation/alkene isomerization/DKP Diels-Alder cycloaddition: To a diketopiperazine (0.2-0.3 mmol) in methanol (1.0-2.0 mL, degassed with nitrogen) at room temperature was added the dieneophilic aldehyde substrate (1.2-1.3 equiv) and a freshly prepared solution of sodium methoxide (3 equiv, 0.45-1.0 mL, 2.0 M). The reaction mixture was heated to 65° C. for 16-24 h. After cooling to room temperature, the reaction mixture was diluted with sat. aqueous NH$_4$Cl (10 mL) and extracted with EtOAc (3×10 mL). The combined organic layers were washed with brine (10 mL), dried (Na$_2$SO$_4$), filtered and concentrated in vacuo.

General Conditions B for aldol condensation/alkene isomerization/DKP Diels-Alder cycloaddition: aldol condensation/alkene isomerization/DKP Diels-Alder cycloaddition. To a diketopiperazine (0.2 mmol) in toluene (2 mL) at −78° C. was added lithium bis(trimethylsilyl)amide (LiHMDS) (1.0M in THF, 1.1 equiv) dropwise over 5 min by syringe. After stirring for 15 min at −78° C., the aldehyde substrate (1.1-2 equiv) was added to the solution. After stirring for an additional 15 min at −78° C., Ac$_2$O (1.3 equiv) was added and the cooling bath removed. The reaction mixture was stirred at room temperature for 1-2 h. 1,8-Diazabicyclo[5.4.0]undec-7-ene (DBU) (2 equiv) was added and the reaction was heated to 90° C. for 16-24 h. After cooling to room temperature, the reaction mixture was diluted with sat. aqueous NH$_4$Cl (20 mL) and extracted with EtOAc (3×15 mL). The organic layers were combined, washed with brine (10 mL), dried (Na$_2$SO$_4$), filtered and concentrated in vacuo.

Example 1

Preparation of the desired DKP derivatives was readily accomplished. For example, the diastereomeric DKP lactim ether products 10 and 11 were obtained in 36% and 19% yield over three steps (two chromatographic separations) starting from N-chloroacyl L-serine methyl ester (Bedurftig, S.; Wunsch, B. *Bioorg. Med. Chem.* 2004, 12, 3299-3311). The absolute structure of major isomer 10 was validated through X-ray crystallographic analysis.

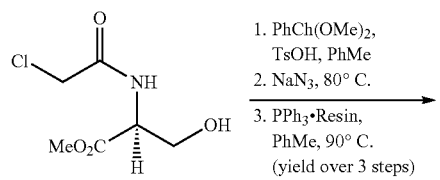

1. PhCh(OMe)$_2$, TsOH, PhMe
2. NaN$_3$, 80° C.
3. PPh$_3$•Resin, PhMe, 90° C. (yield over 3 steps)

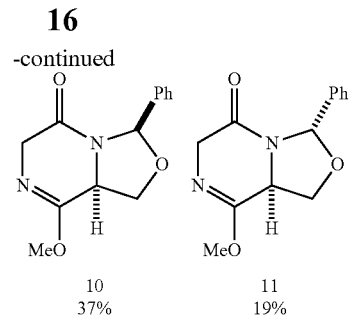

10
37%

11
19%

Diketopiperazine lactim methyl ether 10, 11. To N-chloroacyl L-serine methyl ester (see Bedurftig, S.; Wunsch, B. *Bioorg. Med. Chem.* 2004, 12, 3299-3311) (4.5 g, 22.8 mmol) in toluene (220 ml) at room temperature was added benzaldehyde dimethyl acetal (2.9 ml, 27.4 mmol) and p-toluenesulfonic acid monohydrate (108 mg, 0.57 mmol). The solution was heated at reflux for 16 h with a Dean-Stark trap. After cooling to rt, the solution was diluted with saturated aqueous NaHCO$_3$ (2×50 ml). The organic layer was removed and the aqueous portion extracted with Et$_2$O (75 ml). The combined organic layers were washed with brine (50 ml), dried with Na$_2$SO$_4$, and concentrated in vacuo. The viscous product was purified by flash column chromatography on silica gel (elution: 10% to 60% EtOAc in hexane) to afford a yellow oil (5.48 g, 19.23 mmol, dr ca. 2:1). This intermediate product was dissolved in butanone (110 ml), sodium azide (2.50 g, 38.5 mmol) was added, and the heterogenous mixture was heated to 80° C. for 15 h. After cooling to rt, the mixture was concentrated to a syrup and diluted with a half-saturated NaCl solution (100 ml) and extracted with Et$_2$O (3×50 ml). The combined organic phases were dried with Na$_2$SO$_4$, and concentrated to afford a reddish-brown oil (5.34 g, 18.3 mmol). This intermediate azide product was used without purification in the subsequent Staudinger reduction. After dissolving the intermediate azide product (2.3 g, 7.9 mmol) in toluene (45 ml), resin-bound triphenyl phosphine (3.3 g, ~10.0 mmol) was added at rt. The mixture was stirred for 10 min at rt until gas evolution steadied and was heated to 90° C. for 20 h. Additional resin-bound triphenyl phosphine was added (0.5 g), until consumption the starting material was apparent by TLC. After cooling to rt, the phosphine resin was removed by vacuum filtration. The filtrate was concentrated and purified by flash column chromatography on silica (elution: 30% to 100% EtOAc in hexane) to afford DKP 10 (0.88 g, 36% yield, 3 steps) as a white solid and DKP 11 (0.44 g, 19% yield, 3 steps) as a light yellow oil:

10: mp 133° C.; TLC (60% EtOAc in hexane), Rf: 0.15 (KMnO$_4$); $[\alpha]_D^{25}$=−63.2° (c=2.02, CH$_2$Cl$_2$); IR (film) 3022, 2948, 2872, 1684, 1559, 1361, 1265, 1185, 1048, 934, 760 cm$^{-1}$; $^1$H NMR (400 MHz, CDCl$_3$) 7.37 (m, 3H), 7.29 (m, 2H), 6.25 (s, 1H, C$_8$H), 4.49 (m, 1H), 4.31 (m, 1H), 4.28 (d, J=19.5 Hz, 1H), 4.12 (dd, J=19.9, 3.9 Hz, 1H), 4.04 (t, J=9.0, 1H, C$_6$H), 3.83 (s, 3H); $^{13}$C NMR (100 MHz, CDCl$_3$) δ 166.0, 161.3, 136.9, 129.6, 128.9, 126.8, 90.2, 65.7, 55.1, 54.1, 53.6; Exact mass calcd for C$_{13}$H$_{14}$N$_2$O$_3$Na [M+Na]$^+$, 269.0897. Found 269.0892.

11: TLC (60% EtOAc in hexane), Rf: 0.20 (KMnO$_4$); $[\alpha]_D^{25}$=−107° (c=2.30, CH$_2$Cl$_2$); IR (film) 2993, 2950, 2892, 1704, 1438, 1338, 1315, 1224, 1113, 1011, 850, 769 cm$^{-1}$; $^1$H NMR (400 MHz, CDCl$_3$) 7.50 (m, 3H), 7.40 (m, 2H), 6.50 (s, 1H, C$_8$H), 4.49 (dd, obs triplet, J=6.6 Hz, 1H), 4.37 (m, 1H), 4.23 (s, 2H), 3.88 (t, J=9.0 Hz, 1H, C$_6$H), 3.76 (s, 3H); $^{13}$C NMR (100 MHz, CDCl$_3$) δ 165.4, 158.6, 138.2, 129.3, 128.8, 126.5, 88.9, 69.4, 54.3, 53.8, 52.2; Exact mass calcd for $C_{13}H_{14}N_2O_3Na$ [M+Na]$^+$, 269.0897. Found 269.0901.

We explored the process of Scheme 1 using DKP 10 and alkenal 2 (salicaldehyde allyl ether), easily prepared by alkylation of salicaldehyde. We determined that a domino (Tietze, L. F. *Chem Rev.* 1996, 96, 115-136) reaction sequence with DKP 10 could be initiated under the equilibrating basic conditions of General Conditions A (NaOMe in MeOH at reflux) by enolization and subsequent aldol condensation to give intermediate 50, see Scheme 3 below. Isomerization of the exocyclic alkene in 50 to the endocyclic DKP azadiene in 51 precedes intramolecular Diels-Alder cycloaddition with the terminal alkene to give the observed cycloadduct product 31. The one-pot synthetic operation occurs in good yield (76%) and delivers the product in favorable diastereoselectivity (95:5). The structure of pentacyclic adduct 31 was verified by single crystal X-ray analysis and confirmed that the cycloaddition reaction occurred on the azadiene face opposite the phenyl aminal substituent from the endo transition state.

0.40 (CAM); $[\alpha]_D^{25}=-75.3°$ (c=0.77, MeOH); IR (film) 2948, 2865, 1691, 1633, 1490, 1289 cm$^{-1}$; $^1$H NMR (400 MHz, CDCl$_3$) 7.38-7.35 (m, 3H), 7.32-7.28 (m, 3H), 7.18 (t, J=7.4 Hz, 1H), 7.05 (t, J=7.4 Hz, 1H), 6.97 (d, J=7.8 Hz, 1H), 6.26 (s, 1H), 4.51 (d, J=9.3 Hz), 4.06 (dd, J=11.7, 3.9 Hz, 1H), 4.02 (d, J=9.4 Hz, 1H), 3.63 (s, 3H), 3.49 (d, J=14.9 Hz, 1H), 3.42 (d, J=14.9 Hz, 1H), 3.28 (t, J=11.7 Hz, 1H), 2.77 (m, 1H), 2.35 (dd, J=12.9, 9.8 Hz, 1H), 1.00 (dd, J=12.9, 4.7 Hz, 1H); $^{13}$C NMR (100 MHz, CDCl$_3$) δ 170.5, 168.9, 159.0, 136.4, 132.5, 131.3, 129.2, 128.5, 127.5, 126.3, 123.9, 120.2, 88.4, 70.7, 67.2, 66.0, 62.5, 54.5, 43.0, 36.6, 32.9); HRMS (ES+): Exact mass calcd for $C_{23}H_{22}N_2O_4Na$ [M+Na]$^+$, 413.1472. Found 413.1470.

Example 2

Figure 2:
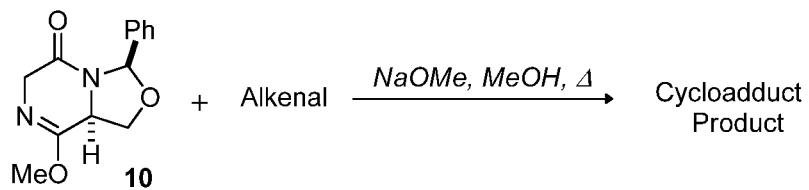
FIG. 2 depicts certain embodiments of the present invention, including several non-enolizable aldehydes reacted with a diketopiperazine under General Procedure A to yield products having a [2.2.2]-diazabicyclic core after undergoing domino reaction sequence described herein.

The reaction described in Scheme 1 was exemplified using a variety of different substrates, some of which are shown in FIG. 2. Aromatic aldehydes such as allyl benzaldehyde (1)

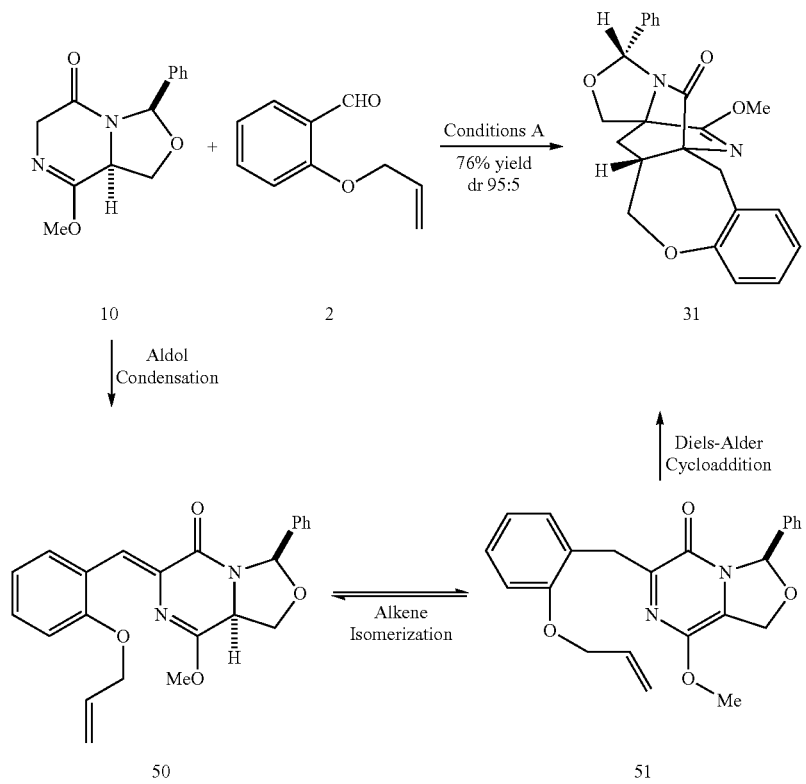

Scheme 3

Cycloadduct 31. Prepared according to General Conditions A. To a solution of DKP 10 (40.4 mg, 0.25 mmol) in methanol (2.0 mL) under nitrogen was added aldehyde 2 (57.1 mg, 0.23 mmol) and sodium methoxide (0.37 mL, 2M, 0.75 mmol). The reaction vessel was fitted with a reflux condenser and heated to 65° C. After stirring at reflux for 21 h, the mixture was cooled to 23° C., diluted with sat. aqueous NH$_4$Cl and extracted with EtOAc (4×15 mL). The combined organic layers were washed with brine, dried with sodium sulfate, and concentrated in vacuo. Purification by flash chromatography on silica gel (elution: 20% to 60% EtOAc in hexane) afforded cycloadduct 31 (68.7 mg, 76% yield) as a colorless amorphous solid: TLC (40% EtOAc in hexane), Rf:

and vinyl benzaldehyde (3, prepared from 1-bromo-2-vinylbenzene via lithium-halogen exchange (n-BuLi) and trapping the derived aryl lithium with DMF (Kleine, T.; Bergander, K.; Froehlich, R.; Wibbeling, B.; Wuerthwein, E.-U. *J. Org. Chem.* 2011, 76, 1979-1991)) proceeded in comparable fashion to Example 1 to give the six- and five-membered carbocyclic ring fused cycloadducts 30 (dr 9:1) and 32 when combined with DKP 10 under General Conditions A. Other non-enolizable aldehydes were competent in the domino reaction sequence with methanolic sodium methoxide (General Conditions A). For example, aldehyde 4 (2,2-Dimethyl-4-pentenal, prepared according to the methods of Magnus et al. (see Magnus, P. D.; Nobbs, M. S. *Synth. Commun.* 1980, 10, 273-278)), bearing a quaternary substitution, provided product 33 in excellent diastereoselectivity.

Figure 3:
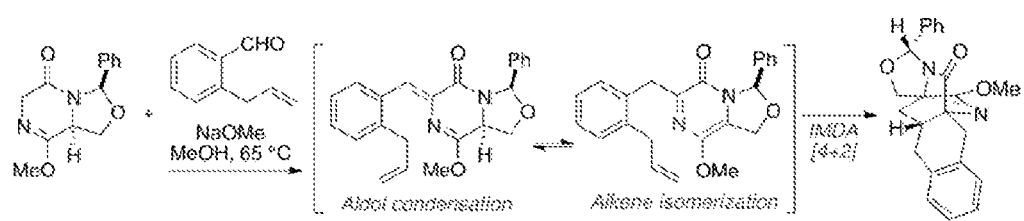
FIG. 3 depicts an example of the claimed process, showing the reactants going through the three-step sequential reaction sequence in a one-pot procedure to produce the [2.2.2]-diazabicyclic product 30.

FIG. 3 shows the reaction sequence for the reaction of allyl benzaldehyde with DKP 10 under General Procedure A. After the initial aldol condensation to give the intermediate shown in FIG. 3, alkene isomerization takes place, setting the stage for the final step of the domino reaction sequence, the intramolecular Diels-Alder reaction, to produce the cycloadduct 30 as a diastereomeric mixture (9:1) in 67% yield.

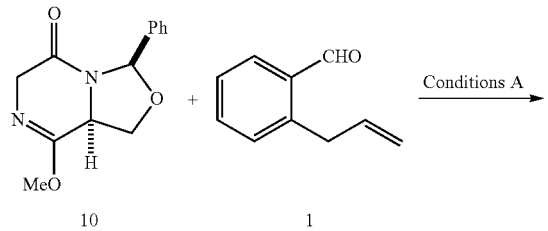

Cycloadduct 30. Prepared according to General Conditions A. The unpurified product was a 90:10 mixture of diastereomers as judged by $^1$H NMR. Purification by flash chromatography on silica gel (elution: 15% to 60% EtOAc in hexanes) afforded cycloadduct product 30 as a white solid (76.8 mg, 68% yield): mp 165.4-168.0° C.; TLC (30% EtOAc in hexane), Rf: 0.25 (CAM); $[\alpha]_D^{25}$=+21.5° (c=0.12, CH$_2$Cl$_2$); IR (film) 3359, 2946, 1684, 1632, 1495, 1453, 1409, 1582, 1337, 1253, 1212, 763, 742; $^1$H NMR (400 MHz, CDCl$_3$) 7.36 (m, 3H), 7.31 (m, 3H), 7.18 (t, J=7.0 Hz, 1H), 7.11 (t, J=7.0 Hz, 1H), 7.04 (d, J=7.4 Hz, 1H), 6.23 (s, 1H), 4.59 (d, J=9.4 Hz, 1H), 4.08, (d, J=9.4 Hz, 1H), 3.77 (s, 3H), 3.74 (d, J=18.0 Hz, 1H), 3.33 (d, J=18.0 Hz, 1H), 2.85 (dd, J=16.0, 5.1 Hz, 1H), 2.55-2.45 (m, 4H), 1.45 (d, J=10.2 Hz, 1H); $^{13}$C NMR (100 MHz, CDCl$_3$) 170.2, 169.5, 136.5, 134.4, 134.2, 129.8, 129.2, 128.5, 128.0, 126.7, 126.3, 126.3, 125.5, 88.4, 67.4, 66.5, 64.1, 62.9, 54.8, 37.6, 36.3, 34.8, 34.2, 33.; Exact mass calcd for (C$_{23}$H$_{22}$N$_2$O$_3$Na) [M+Na]$^+$, 397.1523. Found 397.1525.

Cycloadduct 32. Prepared according to a modified General Conditions A, whereby additional vinyl benzaldehyde (1 equiv, 2.25 equiv total) was added to the reaction mixture after 1 h and the solution was maintained at 65° C. for an additional 18 hours. The reaction vessel was cooled to room temperature and worked up according to the general procedure A. The unpurified product was a single diastereomer as judged by $^1$H NMR. Purification by flash chromatography on silica gel (elution: 10% to 40% EtOAc in hexanes) afforded cycloadduct 32 (49.2 mg, 68% yield) as a pale yellow solid: mp 208° C.; TLC (40% EtOAc in hexane) Rf: 0.30 (CAM); $[\alpha]_D^{25}$=+140° (c=1.70, CH$_2$Cl$_2$); IR (film) 3064, 2950, 2894, 1698, 1639, 1457, 1399, 1369, 1241, 1199, 1072, 841, 755 cm$^{-1}$; $^1$H NMR (400 MHz, CDCl$_3$) 7.37-7.15 (m, 8H), 7.04 (d, J=7.0 Hz, 1H), 6.24 (s, 1H), 4.58 (d, J=9.8 Hz, 1H), 4.11 (d, J=9.8 Hz, 1H), 3.81 (dd, J=10.2, 6.3 Hz, 1H), 3.68 (s, 3H), 3.62 (d, J=15.6 Hz, 1H) 3.36 (d, J=15.6 Hz, 1H), 2.57 (t, J=11.7, 1H), 1.95 (dd, J=12.5, 6.3 Hz, 1H); $^{13}$C NMR (100 MHz, CDCl$_3$) δ 171.4, 142.9, 141.8, 136.3, 129.3, 128.5, 127.0, 126.5, 125.8, 123.0, 88.58, 88.6, 77.9, 67.1, 65.4, 54.7, 49.8, 36.4, 35.5, 32.2; Exact mass calcd for C$_{22}$H$_{20}$N$_2$O$_3$Na [M+Na]$^+$, 383.1366. Found 383.1368.

Cycloadduct 33. Prepared according to General Conditions A. The unpurified product was a single diastereomer as judged by $^1$H NMR. Purification by flash chromatography on silica gel (elution: 20% to 60% EtOAc in hexanes) afforded cycloadduct 33 (34 mg, 50% yield) as a white solid: mp 121.6-123.6° C.; TLC (40% EtOAc in hexanes), Rf: 0.59 (CAM); $[\alpha]_D^{25}$=+46.3° (c=0.88, CH$_2$Cl$_2$); IR (film) 3852, 3748, 2948, 2893, 2863, 1682, 1635, 1558, 1456, 1398, 1353, 1312, 1216, 1197 cm$^{-1}$; $^1$H NMR (400 MHz, CDCl$_3$) 7.35 (m, 3H), 7.26 (m, 2H), 6.18 (s, 1H), 4.49 (d, J=9.4 Hz, 1H), 4.01 (d, J=9.4 Hz, 1H), 3.84 (s, 3H), 2.55 (m, 1H), 2.23 (d, J=13.7 Hz, 1H), 2.18 (dd, J=12.1, 9.4 Hz, 1H), 2.07 (d, J=13.7 Hz, 1H), 1.73 (dd, J=12.1, 7.0 Hz, 1H), 1.42 (dd, J=12.1, 4.7 Hz, 1H), 1.22 (s, 3H), 1.21 (m, 1H), 1.13 (s, 3H); $^{13}$C NMR (100 MHz, CDCl$_3$) δ 170.1, 169.6, 136.6, 129.1, 128.5, 126.4, 88.2, 77.7, 76.7, 67.0, 64.9, 54.5, 46.1, 44.4, 43.3, 39.3, 33.7, 31.9, 31.7; Exact mass calcd C$_{20}$H$_{24}$N$_2$O$_3$Na [M+Na]$^+$, 363.1679. Found 363.1681.

Example 3

Figure 4:
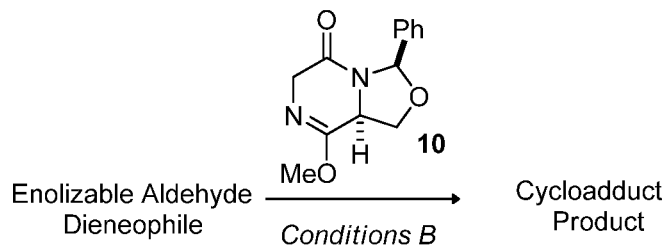
FIG. 4 depicts certain embodiments of the present invention, including several enolizable aldehydes reacted with a diketopiperazine under General Procedure B to yield products having a [2.2.2]-diazabicyclic core after undergoing domino reaction sequence described herein.

Alternate reaction conditions (General Conditions B) were required to effect the aldol condensation, isomerization, and cycloaddition with enolizable aldehyde dieneophile substrates, some examples of which are shown in FIG. 4. For example, the reaction sequence with 5-hexenal (5) was realized by first preparing the enolate of DKP 10 (LiHMDS, −78° C., toluene). Addition of 5-hexenal followed by acetic anhydride and warming to ambient temperatures afforded the intermediate β-acetoxy aldol addition product. Acetate elimination to the exocyclic alkene and isomerization to the reactive endocyclic DKP azadiene Diels-Alder precursor was accomplished under mild conditions with DBU. Although elimination and isomerization were rapid at room temperature, the ensuing intramolecular cycloaddition was slow. In practice, the cycloaddition was driven to completion at elevated temperatures (90° C.). In sum, cycloadduct 34 was prepared from 5-hexenal in one reaction vessel and 52% yield over the reaction sequence, with a greater than 95:5 ratio of diastereomers. The structure of 34 was confirmed by X-ray analysis and the stereochemistry is consistent with cycloadducts derived from non-enolizable aldehydes (e.g., 30, as shown in FIG. 2).

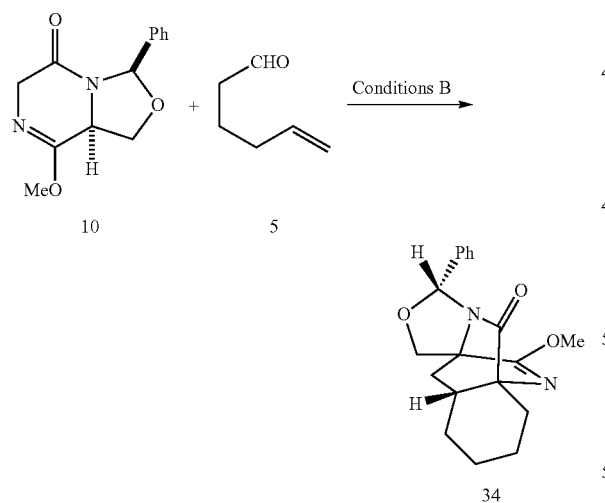

Cycloadduct 34. Prepared according to General Conditions B. The unpurified product was a single diastereomer as judged by $^1$H NMR. Purification by flash chromatography on silica gel (elution: 10% to 50% EtOAc in hexanes) afforded cycloadduct 34 (34.2 mg, 52% yield) as a white solid: mp 148° C.; TLC (40% EtOAc in hexane) Rf: 0.30 (CAM); [α]$_D^{25}$=+118° (c=0.77, MeOH); IR (film) 2923, 2856, 1693, 1637, 1558, 1495, 1456, 1404, 1361, 1208, 1049, 972, 755, 697, 623 cm$^{-1}$; $^1$H NMR (400 MHz, CDCl$_3$) 7.34-7.32 (m, 3H), 7.27-7.24 (m, 2H), 6.20 (s, 1H), 4.51 (d, J=9.4 Hz, 1H), 4.01 (d, J=6.6 Hz, 1H), 3.86 (s, 3H), 2.32 (dd, J=12.5, 9.4 Hz, 1H), 2.16 (m, J=13.6, 1H), 2.04 (m, 1H), 1.90 (m, 1H), 1.83-1.63 (m, 5H), 1.24 (m, 1H), 1.19 (dd, J=12.5, 4.3 Hz, 1H), 1.09 (J=12.9, 3.1 Hz, 1H); $^{13}$C NMR (100 MHz, CDCl$_3$) δ 171.1, 169.0, 136.8, 129.0, 128.5, 126.3, 88.3, 67.3, 67.0, 62.9, 54.4, 38.6, 37.3, 30.2, 29.3, 25.4, 21.0; Exact mass calcd for C$_{19}$H$_{22}$N$_2$O$_3$Na [M+Na]$^+$, 349.1523. Found 349.1524.

General Conditions B proved general for other enolizable aldehydes. Under these conditions, alkenals 6 and 7 delivered cycloadduct products 35 (>95:5 ratio of diastereomers) and 36 (85:15 ratio of diastereomers), respectively. General Conditions B typically afforded somewhat lower product yields than the conditions used for non-enolizable aldehydes. All reactions were stereoselective, though a notable erosion of selectivity was observed with 3,3-dimethyl hexenal (7). The observed cycloadduct product 36 was produced as an 85:15 mixture of diastereomers.

Cycloadduct 35. Prepared according to general procedure B. The unpurified product was a single diastereomer as judged by $^1$HNMR. Purification by flash chromatography on silica gel (elution: 30% to 80% EtOAc in hexanes) afforded cycloadduct 35 (20.2 mg, 31.2%) as a white solid: mp 132.6-133.8° C.; TLC (60% EtOAc in hexanes), Rf: 0.46 (KMnO$_4$); [α]$_D^{25}$=+42.7° (c=0.80, CH$_2$Cl$_2$); IR (film) 2947, 2869, 1689, 1635, 1558, 1540, 1398, 1353, 1317, 1255, 1212, 1196, 1018, 915, 759, 736, 697, 621, 551 cm$^{-1}$; $^1$H NMR (400 MHz, CDCl$_3$) 7.34 (m, 3H), 7.26 (m, 2H), 6.19 (s, 1H), 4.51 (d, J=9.8 Hz, 1H), 4.09 (d, J=9.8 Hz, 1H), 3.83 (s, 3H), 2.34 (m, 2H), 2.22 (dd, J=12.5, 9.5 Hz, 1H), 2.20 (m, 1H), 2.10-1.86 (m, 3H), 1.48 (dd, J=12.5, 5.1 Hz, 1H), 1.26 (m, 1H); $^{13}$C NMR (100 MHz, CDCl$_3$) δ 170.3, 170.1, 136.6, 129.1, 128.5, 126.4, 88.4, 76.7, 67.1, 65.2, 54.6, 45.6, 34.1, 30.0, 28.1, 23.6; Exact mass calculated for C$_{18}$H$_{20}$N$_2$O$_3$Na [M+Na]$^+$, 335.1366. Found 335.1364.

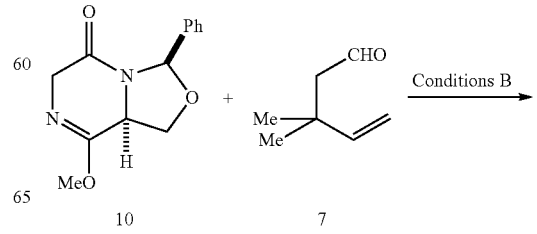

23
-continued

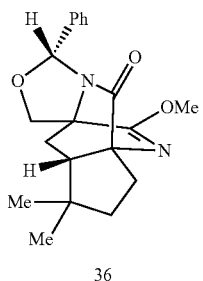

36

Cycloadduct 36. Prepared according to general procedure B. The unpurified product was a 85:15 ratio of diastereomers as judged by ¹H NMR. Purification by flash chromatography on silica gel (elution: 10-50% EtOAc in hexanes) could not separate the diastereomers; cycloadduct 36 (31.5 mg, 44% yield) was afforded as a pale yellow oil (data for major isomer): TLC (40% EtOAc in hexane); Rf: 0.40 (CAM); $[\alpha]_D^{25}$=+24° (c=2.14, $CH_2Cl_2$); IR (film) 2951, 2866, 1683, 1639, 1458, 1398, 1353, 1216, 1029, 936, 738 cm⁻¹; ¹H NMR (400 MHz, $CDCl_3$) 7.32 (m, 3H), 7.25 (m, 2H), 6.17 (s, 1H), 4.51 (d, J=9.4 Hz, 1H), 4.04 (d, J=9.8 Hz, 1H), 3.83 (s, 3H), 2.51 (m, 1H), 2.22 (dd, J=10.2, 6.3 Hz, 1H), 2.15 (m, 1H), 2.11 (dd, J=20.7, 8.6 Hz, 1H), 1.90 (m, 1H), 1.80 (m, J=5.1 Hz, 1H), 1.57 (dd, J=12.5, 6.3 Hz, 1H), 1.04 (s, 3H), 0.87 (s, 3H); ¹³C NMR (100 MHz, $CDCl_3$) δ 170.4, 169.4, 129.0, 128.5, 128.4, 128.4, 126.4, 126.0, 88.2, 77.8, 67.1, 65.9, 55.0, 54.3, 41.7, 39.1, 30.7, 29.5, 27.3, 25.0; Exact mass calcd for $C_{20}H_{24}N_2O_3Na$ [M+Na]⁺, 363.1679. Found 363.1667.

24

Example 4

The chemistry detailed in Scheme 1 and Scheme 2 establishes a clear pathway for the enantioselective synthesis of many members of the [2.2.2]-diazabicyclic natural product family. For example, we initiated a synthesis (see Scheme 4) of (+)-malbrancheamide B (2), a new calmodulin (CaM) inhibitor, to validate our methodology and demonstrate efficient production of this exceptional alkaloid (see Figueroa, M.; Gonzalez, M. D. C.; Mata, R. *Nat. Prod. Res.* 2008, 22, 709-714; Martinez-Luis, S.; Rodriguez, R.; Acevedo, L.; Gonzalez, M. C.; Lira-Rocha, A.; Mata, R. *Tetrahedron* 2006, 62, 1817-1822).

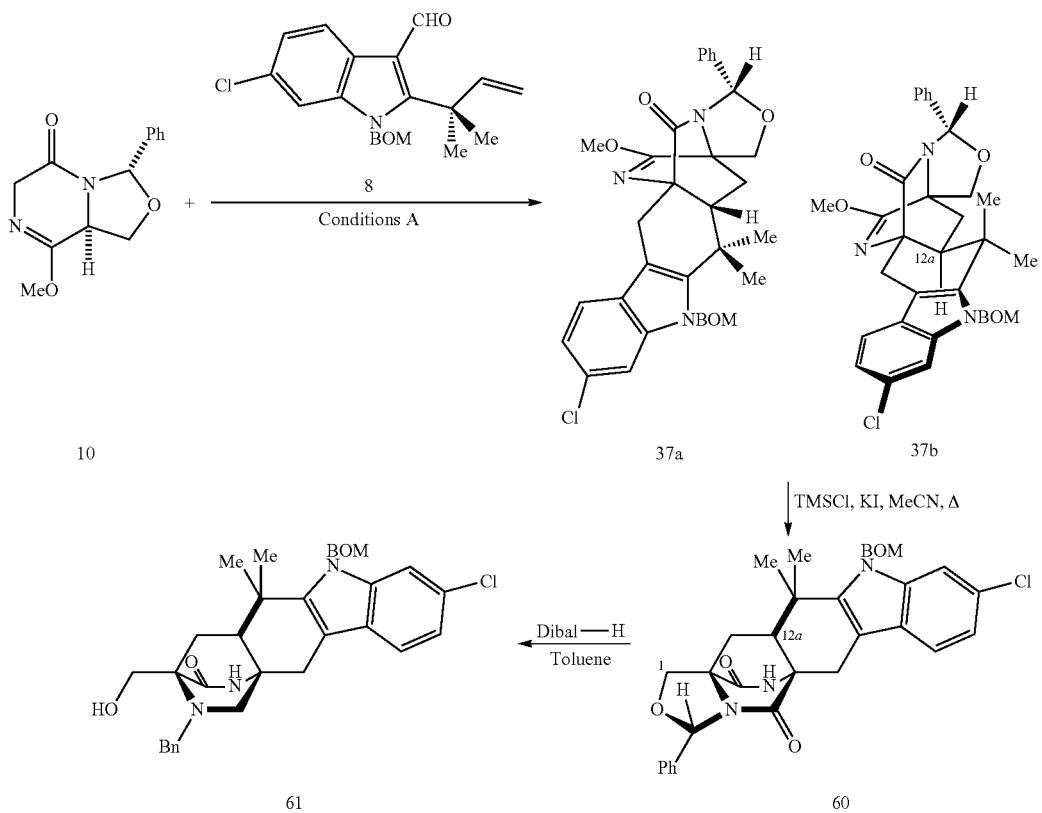

The reverse prenylated indole carboxaldehyde 8 was prepared largely according to precedent (Miller, K. A.; Welch, T. R.; Greshock, T. J.; Ding, Y. S.; Sherman, D. H.; Williams, R. M. *J. Org. Chem.* 2008, 73, 3116-3119).

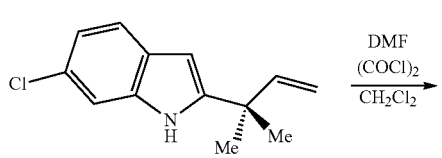

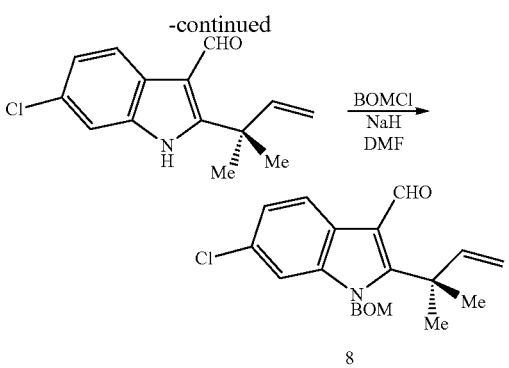

Oxalyl chloride (1.00 mL) was added to DMF (0.95 mL) and CH$_2$Cl$_2$ (31 mL) at 0° C. and the solution was allowed to stir for 15 minutes at 0° C. 6-chloro-2-(2-methylbut-3-en-2-yl)-1H-indole-3-carbaldehyde (see Miller, K. A.; Welche, T. R.; Greshock, T. J.; Ding, Y.; Sherman, D. H.; Williams, R. M. J. Org. Chem. 2008, 73, 3116-3119) (1.641 g, 7.47 mmol) was dissolved in CH$_2$Cl$_2$ (21 mL) and transferred to the oxalyl chloride solution over 2 min via syringe. The reaction mixture was allowed to stir at 0° C. for 5 min and the cooling bath was removed. After stirring 1.5 h at rt, the mixture was concentrated to a volume of ~5 mL and THF (10 mL), NaOH (10 mL), and H$_2$O (10 mL) were added. The biphasic mixture was stirred rapidly for 2 h, Et$_2$O was added (15 mL) and the organic layer removed. The aqueous layer was extracted with additional Et$_2$O (3×15 mL). The combined organic layers were washed with brine, dried (Na$_2$SO$_4$), and concentrated in vacuo. Recrystallization (MeOH/toluene) of the white powder afforded 1-((benzyloxy)methyl)-6-chloro-2-(2-methylbut-3-en-2-yl)-1H-indole-3-carbaldehyde (910 mg, 49% yield) as colorless needles: mp 227° C.; TLC (10% EtOAc in hexane), Rf: 0.40 (CAM); IR (KBr pellet) 1628, 1577, 1457, 1378, 1352, 1294, 1179, 1147, 1102, 1061, 1104, 964, 922 cm$^{-1}$; $^1$H NMR (400 MHz, CDCl$_3$) 10.45 (s, 1H), 8.34 (s, 1H), 8.28 (d, J=8.6 Hz, 1H), 7.35 (d, J=1.6 Hz, 1H), 7.24 (dd, J=8.6, 2.0 Hz, 1H), 6.22 (dd, J=17.6, 10.6 Hz, 1H), 5.32 (d, J=2.0 Hz, 1H), 5.29 (d, J=8.6 Hz, 1H), 1.73 (s, 6H); $^{13}$C NMR (100 MHz, MeOD) 210.2, 188.7, 159.0, 147.5, 137.1, 130.1, 126.9, 124.2, 123.8, 113.5, 112.7, 41.4, 30.8, 29.56. Exact mass calcd for C$_{14}$H$_{14}$ClNONa [M+Na]$^+$, 270.0656. Found 270.0656.

To a dry flask was added NaH (57-63% disp. on oil, 71.2 mg, ca. 1.75 mmol) and DMF (1.6 mL). The reaction vessel was cooled to 0° C. and 1-((benzyloxy)methyl)-6-chloro-2-(2-methylbut-3-en-2-yl)-1H-indole-3-carbaldehyde (141.0 mg, 0.569 mmol) was added as a solid in three portions (gas evolution). The reaction mixture was stirred for 5 min, and then benzyl chloromethyl ether (tech grade 75%, 0.471 mL, 3.39 mmol) and tetrabutyl ammonium iodide (43.7 mg) were added. The mixture was brought to room temperature over 1 h while stirring. The reaction mixture was diluted with saturated aqueous NH$_4$Cl and extracted with EtOAc (4×10 mL). The combined organic portions were washed with brine, dried (Na$_2$SO$_4$), and concentrated in vacuo. The resulting residue was purified by flash chromatography on silica gel (elution: 15% to 30% EtOAc in hexane gradient) to afford the protected indole 8 (185.2 mg, 88% yield) as a light yellow oil: TLC (20% EtOAc in hexane), Rf: 0.45 (CAM); IR (film) 1642, 1608, 1578, 1507, 1474, 1414, 1374, 1333, 1215, 1153, 1133 cm$^{-1}$; $^1$H NMR (400 MHz, CDCl$_3$) 10.66 (s, 1H), 8.43 (d, J=9.0 Hz, 1H), 7.42-7.23 (m, 7H), 6.22 (dd, J=17.2, 10.6 Hz, 1H), 5.55 (s, 2H), 5.12 (d, J=10.6 Hz, 1H), 5.01 (d, J=17.2 Hz, 1H), 4.58 (s, 2H), 1.73 (s, 6H); $^{13}$C NMR (100 MHz, CDCl$_3$) δ 188.4, 154.0, 146.3, 138.0, 136.3, 129.9, 128.7, 128.5, 128.4, 128.1, 124.7, 123.8, 123.7, 117.4, 112.9, 110.2, 73.5, 70.5, 42.0, 30.7. Exact mass calcd for C$_{22}$H$_{22}$ClNO$_2$Na [M+Na]$^+$, 390.1231. Found 390.1232.

Reaction of alkenal 8 with DKP 11 under methanolic sodium methoxide (General Conditions A) afforded a mixture of diastereomeric cycloadducts 37a and 37b (dr 2:1) in 85% combined yield. This reaction outcome demonstrates that the chiral aminal effectively controls the diastereoface of the intramolecular diketopiperazine cycloaddition. It is noteworthy that the major product (37a) resulting from cycloaddition with the reverse prenyl substituent in 8 is diastereomeric (at C12a) to the trend observed for other reaction products illustrated, for example, in FIG. 2.

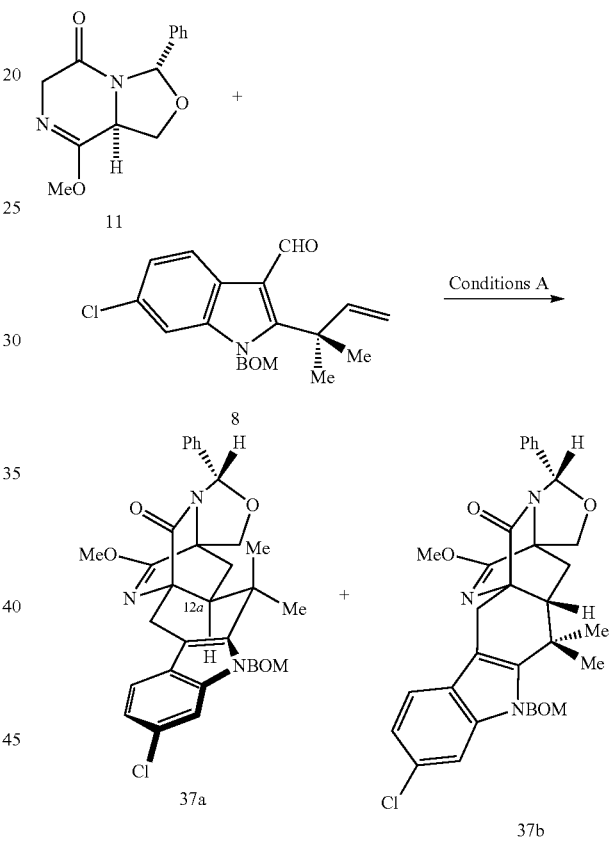

Cycloadduct 37a, 37b. Prepared according to General Conditions A. The unpurified product was a 2:1 ratio of diastereomers as judged by $^1$H NMR. The product was purified by flash chromatography on silica gel (elution: 0% to 45% EtOAc in hexanes) to afford products 37a and 37b (combined 255.1 mg, 85% yield) as a yellow oil: TLC (20% EtOAc in hexane) Rf=0.20 (CAM); [α]$_D^{25}$=−8.8° (c=0.77, CHCl$_3$); IR (film) 1698, 1644, 1475, 1411, 1361, 1311, 1261, 1203, 1066, 885 cm$^{-1}$; $^1$H NMR (400 MHz, CDCl$_3$) 7.44 (d, J=8.2 Hz, 0.5H), 7.40 (d, J=8.2 Hz, 1H), 7.39-7.30 (m, 20H), 7.26-7.23 (m, 2H), 7.19 (d, J=1.6 Hz, 1H), 7.17 (d, J=1.8 Hz, 2H), 7.10 (dd, J=8.2, 1.6 Hz, 2H), 7.06 (dd, J=8.4, 1.6 Hz, 1H), 6.27 (s, 0.5H), 6.19 (s, 1H), 5.66-5.47 (m, 4H), 4.63-4.48 (m, 6.5H), 4.13 (d, J=9.4 Hz, 0.5H), 4.12 (d, J=9.8 Hz, 1H), 3.98 (d, J=16.4 Hz, 1H), 3.86 (s, 3H), 3.76 (s, 1.5H), 3.28 (d, J=17.2 Hz, 0.5H), 3.14 (d, J=16.4 Hz, 1H), 2.54 (dd, J=10.0, 3.7 Hz, 0.5H), 2.45 (dd, J=10.0, 5.3 Hz, 1H), 2.38 (dd, J=13.1, 10.0

Hz, 1H), 2.21 (dd, J=13.1, 5.3 Hz, 1H), 2.17 (s, 1H), 2.07 (dd, J=12.9, 10.2 Hz, 1H), 1.96 (dd, J=12.9, 3.9 Hz, 1H), 1.59 (s, 1H), 1.48 (s, 3H), 1.44 (s, 1.5H), 1.32 (s, 3H), 1.27 (s, 1.5H),; $^{13}$C NMR (100 MHz, CDCl$_3$) δ 171.4, 169.0, 129.2, 129.1, 128.5, 128.5, 128.5, 128.3, 128.0, 128.0, 128.0, 128.0, 126.4, 126.4, 125.6, 120.5, 120.4, 119.5, 119.5, 109.3, 88.7, 88.5, 73.1, 69.8, 67.6, 67.5, 66.8, 63.4, 63.2, 54.7, 54.4, 48.6, 36.8, 31.0, 28.1, 27.8, 27.6, 25.7, 23.8, 21.5; Exact mass calcd for C$_{35}$H$_{34}$ClN$_3$O$_4$Na [M+Na]$^+$, 618.2130. Found 618.2126.

Although 37a and 37b were partially separable by chromatography, it was more convenient to carry the mixture through one additional synthetic operation prior to separation. Correspondingly, as shown in Scheme 4, the lactim methyl ether in 37 was cleaved with TMSI. After chromatographic separation, the derived major bislactam 60a was reduced to aminolactam 61 with excess Dibal at 0° C. (Stocking, E. M.; Sanz-Cervera, J. F.; Williams, R. M. *J. Am. Chem. Soc.* 2000, 122, 1675-1683; Sanz-Cervera, J. F.; Williams, R. M. *J. Am. Chem. Soc.* 2002, 124, 2556-2559). This reduction establishes both the requisite oxidation state of the [2.2.2]-diazabicycle in malbrancheamide B and converts the chiral aminal to a benzyl amine for subsequent elaboration to the natural product.

Diketopiperazine 60a, 60b. To a solution of compounds 37a and 37b (148.7 mg, 0.25 mmol) and potassium iodide (151.0 mg, 0.91 mmol) in acetonitrile (2 mL) was added chlorotrimethylsilane (0.11 mL, 0.87 mmol). The reaction mixture was heated at 80° C. for 1 h, cooled to 23° C., and then 1M NaOH was added. After an additional 1 h of stirring, the aqueous layer was separated and extracted with EtOAc (4×10 mL). The unpurified product was a 2:1 ratio of diastereomers as judged by $^1$H NMR. The product was purified by flash chromatography on silica gel (elution: 30% to 60% EtOAc in hexanes) to afford DKP products 60a (47 mg, 35% yield) and 60b (32 mg, 24%) and mixed fractions (22 mg, 17%; total combined 101 mg, 76% yield) as a white solid: mp 241° C.; TLC (50% EtOAc in hexane) Rf: 0.25 (CAM); [α]$_D^{25}$=−2.7° (c=0.48, MeOH); IR (KBr pellet) 1721, 1690, 1495, 1474, 1453, 1406, 1370, 1311, 1241, 1204, 1109, 1071, 929, 914, 881 cm$^{-1}$; $^1$H NMR (400 MHz, CDCl$_3$) 7.38-7.31 (m, 11H), 7.18 (d, J=1.6 Hz, 1H), 7.08 (dd, J=8.2, 2.0 Hz, 1H), 6.42 (s, 1H), 6.22 (s, 1H), 5.55 (d, J=12.0 Hz, 1H), 5.52 (d, J=12.0 Hz, 1H), 4.77 (d, J=9.4 Hz, 1H), 4.58 (d, J=11.7 Hz, 1H), 4.51 (d, J=11.7 Hz, 1H), 4.14 (d, J=9.8 Hz, 1H), 3.78 (d, J=15.6 Hz, 1H), 2.68 (t, J=7.4 Hz, 1H), 2.66 (d, J=15.6 Hz, 1H), 2.34 (d, J=7.8 Hz, 2H), 1.49 (s, 3H), 1.32 (s, 3H); $^{13}$C NMR (100 MHz, CDCl$_3$) δ 171.5, 166.1, 140.5, 139.1, 136.3, 129.4, 128.6, 128.6, 128.2, 127.9, 126.5, 125.0, 120.8, 119.2, 109.6, 107.2, 89.3, 73.0, 70.0, 68.4, 65.1, 60.8, 50.6, 36.4, 29.9, 27.8, 25.0, 21.0; Exact mass calcd for C$_{26}$H$_{24}$ClN$_3$O$_3$Na [M+Na]$^+$, 484.1398. Found 484.1403.

Aminoalcohol 61. To a solution of DKP 60a (62.5 mg, 0.11 mmol) in toluene (1 mL) at 0° C. was added DIBAL-H (2.10 mL, 1.0 M solution in PhMe). The reaction was stirred for 0.5 h at 0° C., and then EtOAc (2 mL), potassium sodium tartrate tetrahydrate, and water (2 mL) were added. The biphasic mixture was stirred rapidly for 1 h and the organic layer removed. The aqueous layer was extracted with additional EtOAc (3×10 mL). The organic layers were combined, dried (Na$_2$SO$_4$), and concentrated in vacuo. The unpurified product was a single diastereomer as judged by $^1$H NMR. The residue was purified by flash chromatography on silica gel (elution: 45% to 65% EtOAc in hexanes) to afford aminoalcohol 61 (48.8 mg, 80% yield) as a yellow oil: TLC (50% EtOAc in hexane), Rf: 0.75 (CAM); [α]$_D^{25}$=+28.1° (c=3.9, MeOH); IR (film) 1670, 1494, 1474, 1453, 1358, 1314, 1241, 1202, 1146, 1055, 881, 802, 746, 698 cm$^{-1}$; $^1$H NMR (400 MHz, CDCl$_3$) 7.38-7.31 (m, 6H), 7.23-7.15 (m, 7H), 7.05 (dd, J=8.2, 2.0 Hz, 1H), 6.40 (s, 1H), 5.54 (d, J=2.7 Hz, 2H), 4.56 (s, 2H), 4.46 (d, J=12.9 Hz, 1H), 4.18 (dd, J=12.1, 7.8 Hz, 1H), 4.12 (q, J=7.0 Hz, 1H), 3.95 (dd, J=11.7, 5.5 Hz, 1H), 3.49 (t, J=6.4 Hz, 1H), 3.25 (d, J=12.9 Hz, 1H), 3.11 (d, J=10.9 Hz, 1H), 2.87-2.73 (m, 2H), 2.20-2.02 (m, 3H), 1.58 (s, 1H), 1.51 (s, 3H), 1.44 (s, 3H); $^{13}$C NMR (100 MHz, CDCl$_3$) δ 175.0, 141.7, 138.9, 138.7, 136.8, 128.6, 128.4, 128.3, 128.2, 128.0, 127.0, 125.1, 120.8, 118.7, 109.8, 106.6, 77.2, 73.1, 70.2, 64.5, 61.0, 60.0, 58.4, 54.7, 47.5, 35.1, 30.5, 30.2, 29.9, 22.4; Exact mass calcd for C$_{34}$H$_{36}$ClN$_3$O$_3$Na [M+Na]$^+$, 592.2337. Found 592.2338.

Example 5

DKP 13 was synthesized according to the following procedure:

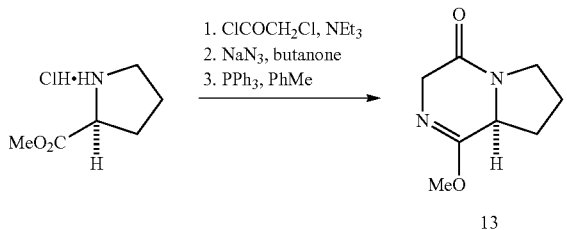

(S)-1-methoxy-6,7,8,8a-tetrahydropyrrolo[1,2-a]pyrazin-4(3H)-one (13). To a suspension of L-proline methyl ester. HCl (8.04 g, 43 mmol) in CH$_2$Cl$_2$ (86.0 ml) at 0° C. was added NEt$_3$ (12.0 mL, 86 mmol), followed by chloroacetyl chloride (1.1 equiv, 3.72 g, 47 mmol) dropwise via syringe. The reaction mixture was allowed to warm to room temperature with stirring. After 16 h, the mixture was diluted with sat. aqueous NaHCO$_3$ and the organic layer was removed. The aqueous portion was extracted with CH$_2$Cl$_2$ (25 mL). The combined organic layers were washed with brine (25 mL), dried (Na$_2$SO$_4$), filtered, and concentrated in vacuo to afford N-chloroacetyl-L-proline methyl ester as a light brown oil (7.85 g, 38 mmol). A portion of the resulting oil (5.25 g, 26 mmol) was dissolved in butanone (51 mL) at RT and NaN$_3$ (3.67 g, 51 mmol) was added in one portion. The reaction vessel was fitted with a reflux condenser and the heterogenous mixture was heated at 80° C. for 20 h. The resulting mixture was cooled to room temperature, filtered and concentrated in vacuo to afford N-azidoacetyl-L-proline methyl ester as a light red oil (5.37 g, 25 mmol). A portion of the oil (1.97 g, 9 mmol) was dissolved in anhydrous PhMe (38 mL) and PPh$_3$ (2.55 g, 10 mmol) was added in one portion. After gas evolution steadied, the reaction mixture was heated at 90° C. for 20 h. The reaction mixture was concentrated in vacuo and triturated with a 1:1 mixture of Et$_2$O/hexanes in order to remove the desired diketopiperazine product from the bulk of phosphine oxide byproduct. The trituration solution was concentrated and the resulting residue was purified by flash column chromatography on silica gel (elution: 1% MeOH to 10% MeOH in 1:1 EtOAc/PhMe+1% NEt$_3$). The resulting diketopiperazine lactim ether product, (S)-1-methoxy-6,7,8, 8a-tetrahydropyrrolo[1,2-a]pyrazin-4(3H)-one (13), (1.43 g, 8 mmol, 80% yield, 3 steps) was obtained as a light yellow oil: TLC (60% EtOAc in hexane), Rf: 0.20 (CAM); [α]$_D^{25}$=+102 (c 2.07, CH$_2$Cl$_2$); IR (film): 2951, 2984, 2889, 2360, 2107, 1685, 1457, 1322, 1263, 1022, 751, 673, 625, 573 cm$^{-1}$; $^1$H NMR (400 MHz, CDCl$_3$) 4.21 (dd, J=9.5 Hz, 1.6 Hz, 1H), 4.11 (d, J=4.9 Hz, 1H) 4.03 (m, 1H), 3.68 (s, 3H), 3.65 (m, 1H) 3.47 (m, 1H), 2.25 (m, 1H), 2.03 (m, 1H), 1.83 (m, 2H);

$^{13}$C NMR (100 MHz, CDCl$_3$) δ 166.4, 161.8, 56.5, 53.3, 52.3, 44.2, 29.3, 22.2; Exact mass calcd for C$_8$H$_{12}$N$_2$O$_2$ [M+Na$^+$], 191.0791. Found 191.0790.

Utilizing General Conditions A, alkenal 8 and DKP 13 were combined in refluxing methanolic sodium methoxide. The reaction proceeded in accordance with Scheme 1 to yield [2.2.2.]-diazabicyclic products 38a, 38b, and 39.

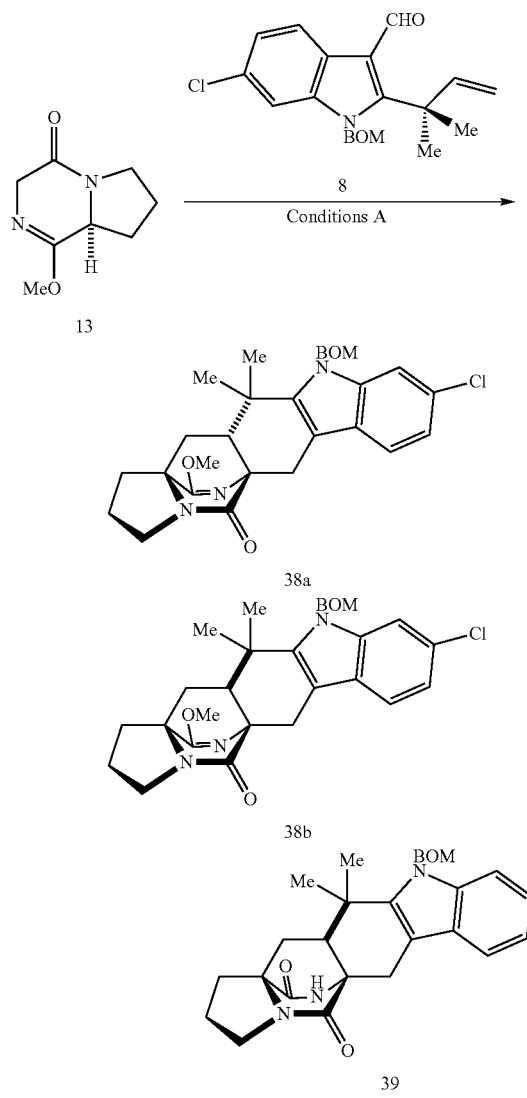

Cycloadduct 38a: (light yellow oil) TLC (5% MeOH in CHCl$_3$), Rf: 0.55 (CAM); IR (film) 1685, 1633, 1476, 1419, 1354, 1324, 1260, 1205, 1179, 1092, 1077, 1055, 1001, 920, 886, 838, 799, 740, 702 cm$^{-1}$; $^1$H NMR (400 MHz, CDCl3) 7.50 (d, J=8.2 Hz, 1H), 7.38-7.30 (m, 5H), 7.19 (s, 1H), 7.10 (dd, J=8.2, 1.6 Hz, 1H), 5.59 (d, J=11.3 Hz, 1H), 5.53 (d, J=11.3 Hz, 1H), 4.56 (d, J=11.7 Hz, 1H), 4.50 (d, J=11.7 Hz, 1H), 3.91 (d, J=17.6 Hz, 1H), 3.71 (s, 3H), 3.54-3.43 (m, 2H), 3.28 (d, J=17.2 Hz, 1H), 2.71-2.64 (m, 1H), 2.41 (dd, J=9.6, 4.1 Hz, 1H), 2.09-1.84 (m, 5H), 1.39 (s, 3H), 1.23 (s, 3H); $^{13}$C NMR (100 MHz, CDCl$_3$) δ 172.2, 170.9, 141.3, 139.3, 137.3, 128.8, 128.2, 128.1, 126.4, 120.6, 120.0, 109.5, 109.4, 73.3, 70.0, 66.8, 64.4, 54.6, 47.6, 43.8, 36.9, 34.5, 29.3, 27.9, 26.4, 24.9, 24.1. Exact mass calcd for C$_{30}$H$_{32}$ClN$_3$O$_3$Na [M+Na]$^+$, 540.2024. Found 540.2017.

Cycloadduct 38b: (light yellow oil) TLC (5% MeOH in CHCl$_3$), Rf: 0.52 (CAM); IR (film) 1678, 1638, 1475, 1419, 1356, 1310, 1265, 1200, 1060, 882, 800, 736, 699 cm$^{-1}$; $^1$H NMR (400 MHz, CDCl$_3$) 7.46 (d, J=8.2 Hz, 1H), 7.39-7.30 (m, 5H), 7.18 (d, J=1.6 Hz, 1H), 7.09 (dd, J=8.2, 2.0 Hz, 1H), 5.55 (d, J=5.1 Hz, 2H), 4.56 (d, J=12.1 Hz, 1H), 4.48 (d, J=12.1 Hz, 1H), 3.99 (d, J=16.4 Hz, 1H), 3.80 (s, 3H), 3.51-3.33 (m, 2H), 3.08 (d, J=16.4 Hz, 1H), 2.68-2.66 (m, 1H), 2.34 (dd, J=10.4, 5.1 Hz, 1H), 2.04-1.92 (m, 4H), 1.83 (dd, J=12.9, 5.1 Hz, 1H), 1.42 (s, 3H), 1.18 (s, 3H); $^{13}$C NMR (100 MHz, CDCl$_3$) δ 172.9, 171.3, 140.7, 139.1, 137.1, 128.5, 128.0, 127.9, 125.7, 120.4, 119.6, 109.9, 109.2, 73.1, 69.7, 65.5, 64.3, 54.5, 54.5, 48.8, 43.4, 36.7, 32.8, 29.3, 27.8, 24.8, 21.4.

Cycloadduct 38c: (colorless solid) mp 224.2-225.6° C.; TLC (5% MeOH in CHCl$_3$), Rf: 0.50 (CAM); IR (KBr pellet) 3199, 1691, 1475, 1455, 1199, 1098, 1058, 883, 811, 733, 697 cm$^{-1}$; $^1$H NMR (400 MHz, DMSO) 8.76 (s, 1H), 7.57 (s, 1H), 7.44 (d, J=8.6 Hz, 1H), 7.37-7.28 (m, 5H), 7.10 (dd, J=8.6, 2.0 Hz, 1H), 5.69 (d, J=10.9 Hz, 1H), 5.64 (d, J=10.9 Hz, 1H), 4.59 (s, 2H), 3.44 (d, J=15.6 Hz, 1H), 3.35 (s, 1H), 3.33-3.23 (m, 1H), 2.72 (d, J=16.0 Hz, 1H), 2.55-2.50 (m, 2H), 2.12-1.81 (m, 5H), 1.36 (s, 3H), 1.09 (s, 3H); $^{13}$C NMR (100 MHz, DMSO) δ 173.0, 168.2, 141.5, 138.6, 137.5, 128.3, 127.7, 127.7, 126.8, 125.0, 120.0, 119.1, 109.8, 107.2, 73.1, 69.0, 66.1, 58.9, 50.2, 43.6, 35.8, 30.5, 28.6, 27.1, 24.0, 23.6, 20.3. Exact mass calcd for C$_{29}$H$_{30}$ClN$_3$O$_3$Na [M+Na]$^+$, 526.1868. Found 526.1862

Example 6

The reaction described in Scheme 2, utilizing an alkyne, an aldehyde, and a DKP, was demonstrated with DKP 10 and 5-hexynal (21) using General Conditions B. 5-Hexynal was prepared from 5-hexyn-1-ol by Parikh-Doering oxidation (SO$_3$.pyr, DMSO, i-Pr$_2$Net, see see Amoroso, J. W.; Borketey, L. S.; Prasad, G.; Schnarr, N. A. Org. Lett. 2010, 12, 2330-2333)). The enolate of DKP 10 was prepared using LiHMDS at −78° C. in toluene. Addition of hexynal followed by acetic anhydride and warming to ambient temperature afforded the aldol addition product. After stirring at room temperature, DBU was added and heat was applied to drive the Diels-Alder condensation. The cycloadduct 41 was obtained as a >95:5 mixture of diastereomers in 40% yield.

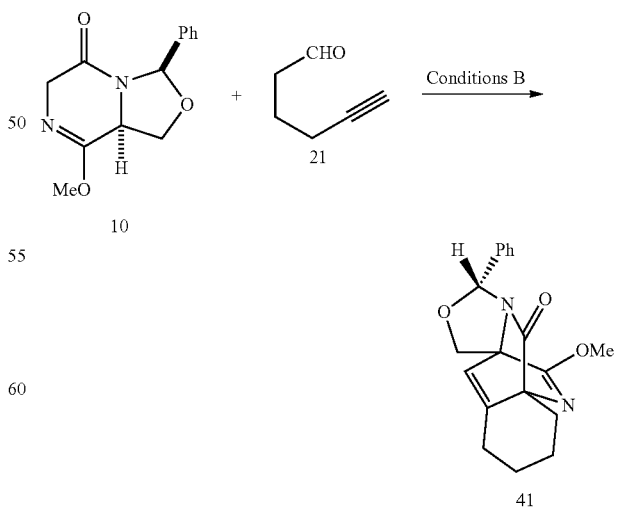

Cycloadduct 41. Purification by flash chromatography on silica gel (elution: 10% to 50% EtOAc in hexanes) afforded product 41 (23.9 mg, 40% yield) as a yellow oil: TLC (40% EtOAc in hexane) Rf=0.40 (CAM); $[\alpha]_D^{25}$=+59° (c=2.70, MeOH); IR (film) 3312, 3064, 2946, 2864, 2366, 1691, 1559, 1268, 1110, 1028, 735 cm$^{-1}$; $^1$H NMR (400 MHz, CDCl$_3$) 7.33 (m, 3H), 7.26 (m, 2H), 6.26 (s, 1H), 5.86 (s, 1H), 4.73 (d, J=9.4 Hz, 1H), 4.31 (d, J=9.8 Hz, 1H), 3.84 (s, 3H), 2.67 (m, 1H), 2.52-2.36 (m, 2H), 2.12 (m, 1H), 1.81-1.66 (m, 3H), 1.61 (m, 1H); $^{13}$C NMR (100 MHz, CDCl$_3$) δ 174.1, 169.2, 155.4, 129.2, 128.4, 126.6, 126.1, 87.9, 74.6, 68.6, 66.9, 66.1, 55.7, 26.9, 25.9, 20.9, 19.3; Exact mass calcd for C$_{19}$H$_{20}$N$_2$O$_3$Na [M+Na]$^+$, 347.1366. Found 347.1355.

Example 7

DKP 12 was synthesized as follows:

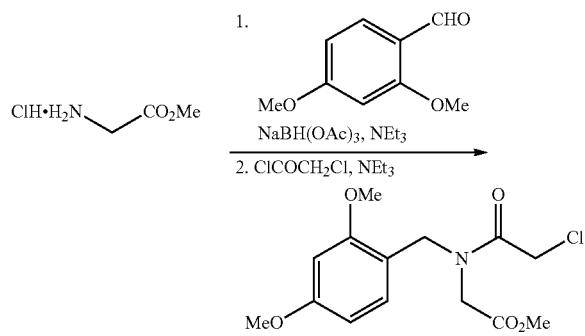

Methyl 2-(2-chloro-N-(2,4-dimethoxybenzyl)acetamido)acetate. A reaction flask was charged with 2-4-dimethoxybenzaldehyde (0.88 g, 5.34 mmol) and dissolved in CH$_2$Cl$_2$ (40 ml) and to the solution was added Et$_3$N (1.1 ml, 7.96 mmol), glycine-methyl ester hydrochloride (1.0 g, 7.96 mmol) and NaB(OAc)$_3$H (2.2 g, 10.7 mmol). The slurry was vigorously stirred for 24 h at room temperature. The reaction mixture was quenched with the addition of saturated aqueous NaHCO$_3$ and the mixture was transferred to a separatory funnel. The organic layer was removed and the aqueous portion was extracted with CH$_2$Cl$_2$ (3×, 100 ml). The organic portions were combined, washed with brine, dried with sodium sulfate, filtered, and concentrated in vacuo to yield a clear oil (1.3 g, 5.44 mmol). The resulting product was dissolved in CH$_2$Cl$_2$ (15 ml) and cooled to 0° C. Chloroacetyl chloride (0.45 ml, 5.71 mmol) and Et$_3$N (0.83 ml, 5.98 mmol) were added dropwise and the reaction mixture was warmed to RT and stirred for 18 h. The reaction mixture was filtered through celite and the filtrate was washed with saturate aqueous NaHCO$_3$. The organic layer was dried with sodium sulfate, filtered, and concentrated in vacuo. The resulting residue was purified by flash column chromatography on silica gel (elution: 25% to 85% EtOAc in hexanes) to afford the desired methyl 2-(2-chloro-N-(2,4-dimethoxybenzyl)acetamido)acetate product as a light orange oil (1.4 g, 4.44 mmol, 57% yield over the 2 steps): IR (film) 3002, 2953, 2839, 2361, 1749, 1662, 1614, 1589, 1509, 1457, 1440, 1420, 1367, 1294, 1267, 1210, 1159, 1130, 1033, 998, 939, 835, 792, 709, 668, 636 cm$^{-1}$. $^1$H NMR (400 MHz, CDCl$_3$) 7.25 (d, J=8.2, 1H), 7.03 (d, J=8.5, 1H), 6.46 (s, 1H), 6.44-6.41 (m, 1H), 4.58 (s, 1H), 4.52 (s, 2H), 4.35 (s, 2H), 4.11 (s, 2H), 4.03 (s, 1H), 4.02 (s, 2H), 3.80 (s, 3H), 3.77 (s, 3H), 3.76 (s, 1H), 3.70 (s, 1H), 3.69 (s, 3H); $^{13}$C NMR (100 MHz, CDCl$_3$), δ 169.3, 167.1, 161.2, 158.7, 131.9, 130.1, 115.3, 104.2, 103.9, 98.8, 98.2, 55.4, 52.4, 52.1, 48.9, 48.2, 46.5, 45.0, 41.3

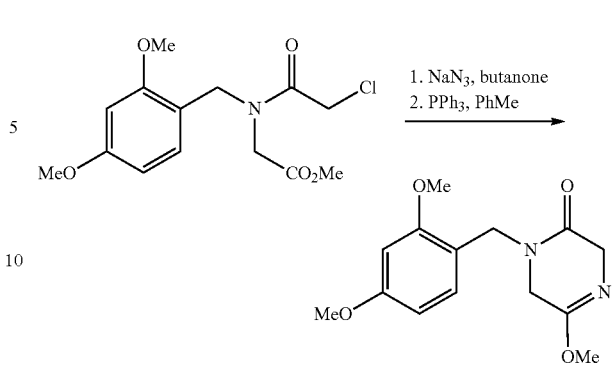

1-(2,4-dimethoxybenzyl)-5-methoxy-1,6-dihydropyrazin-2(3H)-one (12). Methyl 2-(2-chloro-N-(2,4-dimethoxybenzyl)acetamido)acetate (1.4 g, 4.44 mmol) was dissolved in butanone (18 ml), NaN$_3$ (0.58 g, 8.89 mmol) was added, and the mixture was brought to reflux with rapid stirring for 72 h. The reaction mixture was cooled to room temperature, filtered through celite and concentrated in vacuo to yield a yellow oil (1.1 g, 3.5 mmol, 79% yield). The intermediate product was dissolved in toluene (28 ml) and PPh$_3$ (0.97 g, 3.68 mmol) was added. The mixture was heated to 90° C. with stirring. After 19 h, the reaction solution was cooled to room temperature and concentrated in vacuo. The resulting residue was purified by flash column chromatography on silica gel (elution: 25% to 100% EtOAc in hexanes) to provide the DKP 1-(2,4-dimethoxybenzyl)-5-methoxy-1,6-dihydropyrazin-2(3H)-one (12) as a light yellow solid (0.54 g, 1.94 mmol, 56% yield): Rf 0.12 (60% EtOAc in hexane); IR (film) 3852, 3798, 3745, 2947, 2838, 2364, 1843, 1702, 1654, 1589, 1508, 1458, 1325, 1292, 1244, 1210, 1158, 1129, 1098, 1066, 1034, 1009, 938, 835, 776, 756, 668 cm$^{-1}$; $^1$H NMR (400 MHz, CDCl$_3$) 7.22 (d, J=8.6 Hz, 1H), 6.47 (m, 1H), 6.45 (s, 1H), 4.58 (s, 2H), 4.17 (d, J=2.7, 2H), 3.85 (d, J=2.7, 2H), 3.81 (s, 3H), 3.80 (2, 3H), 3.67 (s, 3H); $^{13}$C NMR (100 MHz, CDCl$_3$), δ 166.3, 160.9, 159.0, 158.4, 131.8, 116.4, 104.7, 98.6, 55.6, 53.1, 50.7, 45.9, 43.3.

DKP 12 was combined with alkynal 20 under General Conditions B to yield the cycloadduct 40.

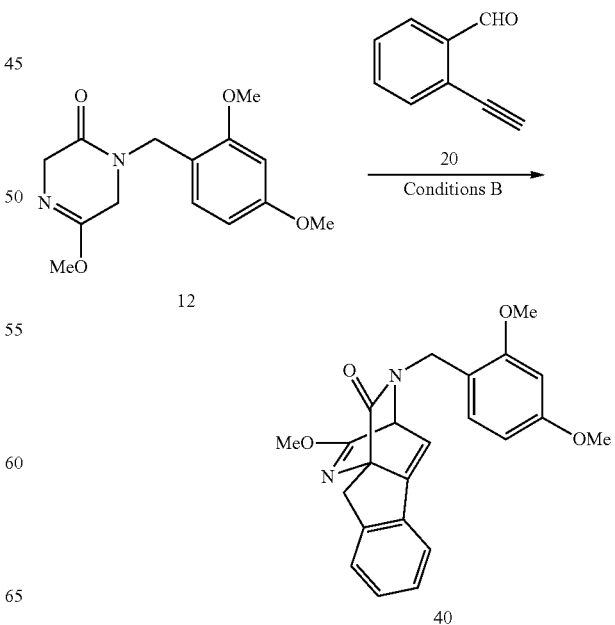

Cycloadduct 40. Purification by flash chromatography on silica gel afforded product 40 in 54% yield: IR (film) 3002.1, 2945.4, 2836.6, 1684.0, 1614.8, 1589.2, 1506.9, 1465.6, 1439.2, 1417.4, 1333.7, 1306.1, 1265.7, 1210.1, 1160.0, 1035.8, 992.0, 934.1, 835.1, 756.0, 735.5, 639.4; $^1$H NMR (400 MHz, CDCl$_3$) 7.39 (d, J=7.42, 1H), 7.30 (t, J=8.20, 2H), 7.18 (t, J=7.42, 2H), 7.04 (d, J=8.60, 1H), 6.47 (d, J=5.47, 1H), 6.44-6.39 (m, 2H), 4.81 (d, J=5.47, 1H), 4.46 (d, J=8.60, 1H), 4.45 (d, J=37.5, 1H), 3.37 (d, J=18.0, 1H), 3.81 (s, 3H), 3.79 (s, 3H), 3.70 (s, 3H), 3.50 (d, J=17.6, 1H). $^{13}$C NMR (100 MHz, CDCl$_3$) δ 174.7, 171.1, 160.6, 158.6, 158.5, 147.6, 133.6, 131.1, 129.9, 126.8, 126.1, 122.0, 116.7, 115.4, 104.0, 98.3, 79.0, 59.2, 55.3, 55.2, 43.7, 35.5; Exact mass calculated for C$_{22}$H$_{23}$O$_4$N$_2$Na$^+$, 413.147178. Rf; 0.45 (60% EtOAc in hexanes).

Similarly, DKP 12 was combined with alkynal 23 under General Conditions B to yield cycloadduct 42.

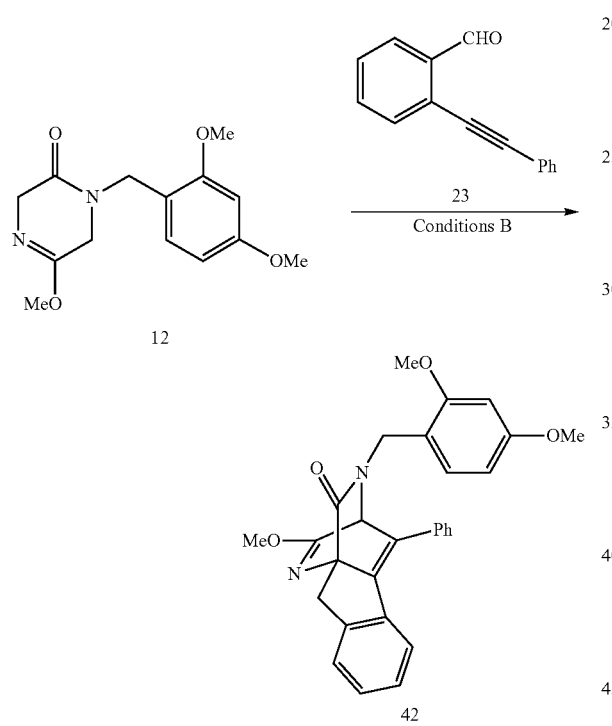

Cycloadduct 42. Purification by flash chromatography on silica gel afforded product 42 in 72% yield: IR (film) 3744.8, 3021.6, 3009.4, 2944.6, 2836.4, 1695.8, 1616.6, 1613.4, 1588.6, 1509.6, 1496.3, 1464.9, 1414.8, 1332.8, 1331.3, 1310.5, 1292.4, 1209.8, 1209.6, 1165.9, 1159.2, 1139.2, 1110.9, 1037.0, 1034.7, 991.2, 930.2, 835.2, 761.0, 753.7, 732.3; $^1$H NMR (400 MHz, CDCl$_3$) 7.41 (d, J=7.82, 1H), 7.38 (d, J=7.82, 1H), 7.33-7.28 (m, 3H), 7.23 (d, J=0.8, 1H), 7.22 (d, J=0.8, 1H), 7.12-7.07 (m, 3H), 7.03-6.99 (m, 1H), 6.38 (dd, J=8.2, 2.3, 1H), 6.29 (d, J=2.3, 1H), 5.00 (s, 1H), 4.54 (dd, J=14.5, 93.0, 2H), 4.41 (d, J=17.8, 1H), 3.76 (s, 3H), 3.75 (s, 3H), 3.58 (s, 3H); $^{13}$C NMR (100 MHz, CDCl$_3$) δ 174.8, 170.9, 160.8, 158.4, 149.9, 147.8, 135.4, 133.8, 132.5, 131.5, 129.7, 128.4, 127.8, 127.3, 126.4, 126.0, 122.2, 166.6, 104.3, 98.3, 79.5, 64.6, 55.3, 55.3, 54.9, 43.2, 35.5; Exact mass calculated for C$_{29}$H$_{26}$N$_2$O$_4$Na+, 489.178478. Rf; 0.40 (40% EtOAc in hexanes).

Similarly, DKP 12 was combined with alkynal 24 under General Conditions B to yield cycloadduct 43.

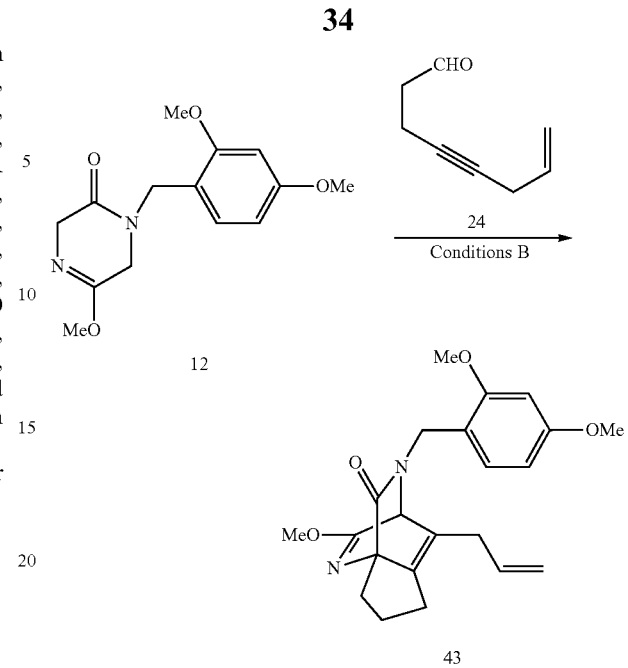

Cycloadduct 43. Purification by flash chromatography on silica gel afforded product 43: TLC (40% EtOAc in hexanes), Rf: 0.25 (CAM); H NMR (400 MHz, CDCl$_3$); 6.94 (d, 1H, J=7.82 Hz), 6.37 (s, 1H), 6.35 (d, 1H, J=7.03 Hz), 5.52 (m, 1H), 4.94 (s, 2H, J=10.16), 4.75 (d, 1H J=1.56), 4.37 (s, 1H), 4.30 (m, 2H), 3.73(s, 3H), 3.72 (s, 3H), 3.60 (s, 3H), 2.88 (m, 1H), 2.68 (dd, 1H, J=15.6/6.25), 2.52 (dd, 1H, J=15.6/6.64 Hz), 2.25 (m, 1H). 2.14 (m, 1H), 2.06-1.96 (m, 2H), 1.70 (m, 1H); $^{13}$C NMR (100 MHz, CDCl$_3$) δ 175.3, 171.8, 160.6, 158.4, 151.8, 133.9, 131.0, 130.6, 116.9, 116.6, 104.0, 98.1, 79.7, 61.1, 55.2, 55.0, 54.9, 42.8, 34.2, 30.0, 26.2, 26.1; HRMS (ES+): Exact mass calculated for C$_{22}$H$_{26}$N$_2$O$_4$Na [M+Na]$^+$ 405.1784 Found 405.1784.

Example 8

DKP 13 was combined with benzaldehyde and alkyne 22, in accordance with Scheme 2, using General Conditions B, to yield cycloadduct 44. Note that in this case, the starting aldehyde and alkyne are separate reactants, i.e., they are not connected at the outset.

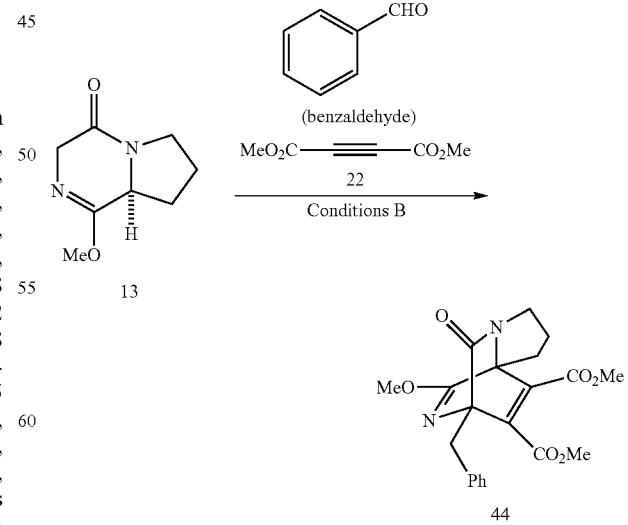

Cycloadduct 44. Purification by flash chromatography on silica gel afforded product 44: TLC (60% EtOAc in hexanes), Rf: 0.60 (KMnO$_4$); IR (film) cm$^{-1}$; H NMR (400 MHz, CDCl$_3$) 7.57-7.55 (d, 2H, J=7.0 Hz), 7.27-7.16 (m, 3H), 3.88 (s, 3H), 3.71 (s, 3H), 3.67 (d, 1H), 3.45 (s, 3H), 3.18 (m, 1H), 2.80 (m, 1H), 2.49 (m, 1H), 2.04 (m, 1H), 1.91 (m, 1H); $^{13}$C NMR (100 MHz, CDCl$_3$) δ 174.2, 168.2, 164.9, 162.4, 152.3, 138.0, 136.6, 130.8, 127.5, 126.3, 74.3, 68.3, 56.4, 52.3, 52.2, 43.0, 35.0, 25.9, 25.2; HRMS (ES+): Exact mass calcd for C$_{21}$H$_{22}$N$_2$O$_6$Na [M+Na]$^+$ 421.1370 Found 421.1365.

Example 9

DKP 13 was combined with alkynal 25 under General Conditions B to yield the cycloadduct 45. in 46% yield: IR (film) 3854.4, 3744.8, 3268.9, 2984.3, 2951.3, 2878.9, 1734.6, 1675.5, 1616.9, 1453.6, 1436.8, 1339.1, 1302.9, 1248.8, 1220.8, 1175.2, 1107.2, 1040.9, 1006.0, 915.8, 841.3, 755.4, 736.1; $^1$H NMR (400 MHz, CDCl$_3$) 7.39 (d, J=7.42, 1H), 7.34 (d, J=7.82, 1H), 7.30 (d, J=7.43, 1H), 7.20 (t, J=7.43, 1H), 6.45 (s, 1H), 4.32 (d, J=17.6, 1H), 3.77 (s, 3H), 3.51 (d, J=18.0, 1H), 3.43-3.39 (m, 1H), 3.27-3.22 (m, 1H), 2.83-2.76 (m, 1H), 2.31-2.24 (m, 1H), 2.18-2.12 (m, 1H), 2.09-2.04 (m, 1H). $^{13}$C NMR (100 MHz, CDCl$_3$) δ 174.8, 169.5, 159.8, 147.5, 133.4, 129.8, 126.8, 126.0, 121.9, 119.7, 80.4, 70.4, 55.5, 42.1, 34.9, 27.0, 25.4; Exact mass calcd for C$_{17}$H$_{16}$N$_2$O$_2$Na$^+$, 303.110399. Rf; 0.20 (40% EtOAc in hexanes).

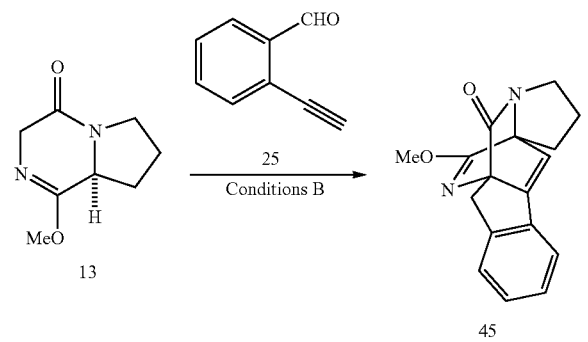

Cycloadduct 45. Purification by flash chromatography on silica gel afforded product 45 in 46% yield: IR (film) 3854.4, 3744.8, 3268.9, 2984.3, 2951.3, 2878.9, 1734.6, 1675.5, 1616.9, 1453.6, 1436.8, 1339.1, 1302.9, 1248.8, 1220.8, 1175.2, 1107.2, 1040.9, 1006.0, 915.8, 841.3, 755.4, 736.1; $^1$H NMR (400 MHz, CDCl$_3$) 7.39 (d, J=7.42, 1H), 7.34 (d, J=7.82, 1H), 7.30 (d, J=7.43, 1H), 7.20 (t, J=7.43, 1H), 6.45 (s, 1H), 4.32 (d, J=17.6, 1H), 3.77 (s, 3H), 3.51 (d, J=18.0, 1H), 3.43-3.39 (m, 1H), 3.27-3.22 (m, 1H), 2.83-2.76 (m, 1H), 2.31-2.24 (m, 1H), 2.18-2.12 (m, 1H), 2.09-2.04 (m, 1H). $^{13}$C NMR (100 MHz, CDCl$_3$) δ 174.8, 169.5, 159.8, 147.5, 133.4, 129.8, 126.8, 126.0, 121.9, 119.7, 80.4, 70.4, 55.5, 42.1, 34.9, 27.0, 25.4; Exact mass calculated for C$_{17}$H$_{16}$N$_2$O$_2$Na$^+$, 303.110399. Rf; 0.20 (40% EtOAc in hexanes).

Similarly, DKP 13 was combined with alkynal 23 under General Conditions B to yield cycloadduct 46.

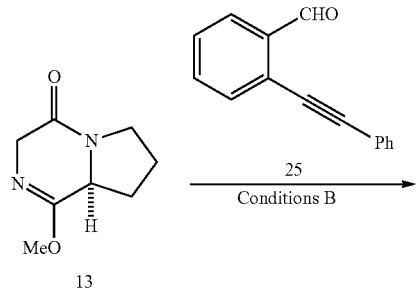

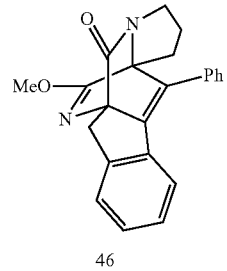

Cycloadduct 46. Purification by flash chromatography on silica gel afforded product 46 in 43% yield: IR (film) 3052.3, 3020.1, 2975.0, 2882.7, 1691.2, 1685.1, 1622.4, 1464.8, 1442.1, 1399.1, 1323.5, 1209.1, 1286.6, 1221.9, 1173.5, 1128.5, 1006.7, 814.5, 754.6, 742.7, 702.1, 611.1; $^1$H NMR (400 MHz, CDCl$_3$) 7.28-7.43 (m, 2H), 7.41-7.36 (m, 2H), 7.24-7.18 (m, 3H), 6.95 (s, 2H), 4.37 (d, J=18.0, 1H), 3.88 (s, 3H), 3.53 (d, J=18.0, 1H), 3.48-3.46 (m, 1H), 3.27-3.24 (m, 1H), 2.58-3.55 (m, 1H), 2.02-1.93 (m, 3H). $^{13}$C NMR (100 MHz, CDCl$_3$) δ 175.5, 170.2, 153.2, 148.0, 135.2, 134.3, 134.3, 132.0, 129.9, 129.1, 129.0, 128.3, 126.8, 126.3, 122.7, 80.2, 77.6, 56.2, 53.7, 42.9, 35.4, 25.8, 21.3; Exact mass calculated for C$_{23}$H$_{20}$N$_2$O$_2$Na$^+$, 379.141699. Rf; 0.20 (40% EtOAc in hexanes).

INCORPORATION BY REFERENCE

All publications, patents, and patent applications cited herein are hereby expressly incorporated by reference in their entirety and for all purposes to the same extent as if each was so individually denoted.

EQUIVALENTS

While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

The articles "a" and "an" are used herein to refer to one or to more than one (i.e. to at least one) of the grammatical object of the article. By way of example, "a reaction" means one reaction or more than one reaction.

Any ranges cited herein are inclusive, e.g., "between five percent and seventy-five percent" includes percentages of 5% and 75%.

I claim:
1. A process for preparing [2.2.2.]-diazabicyclic structures comprising:
reacting a diketopiperazine, an aldehyde, and a substituted unsaturated hydrocarbon under basic conditions to perform a three-step reaction sequence comprising the following sequential steps:
A) performing an aldol condensation,
B) performing an alkene isomerization, and
C) performing a Diels-Alder cycloaddition to form a [2.2.2.]-diazabicyclic structure;
wherein said sequential aldol condensation, alkene isomerization, and Diels-Alder cycloaddition are performed in one reaction vessel without purification and isolation of the products between the sequential reaction steps.
2. The process of claim 1, wherein said aldehyde and said substituted unsaturated hydrocarbon are connected as part of the same molecule.

3. The process of claim 1, wherein the base used to impart said basic conditions is selected from the group consisting of hydrides, carbonates, alkoxides, phenoxides, amides, carbanions, and silyl anions.

4. The process of claim 1, wherein said aldehyde is enolizable.

5. The process of claim 4, wherein the base used to impart said basic conditions is selected from the group consisting of hydrides, amides, carbanions, and silyl anions.

6. The process of claim 1, wherein said diketopiperazine is represented by the formula:

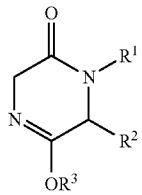

wherein $R^1$ represents hydrogen, alkyl, aryl, substituted alkyl or substituted aryl;

wherein $R^2$ represents hydrogen, alkyl, aryl, substituted alkyl, substituted aryl, a heteroatom, carbonyl, amido, or alkoxyl; and wherein $R^3$ represents alkyl, aryl, substituted alkyl, or substituted aryl.

7. The process of claim 1, wherein said aldehyde is represented by the formula $R^4CHO$, and wherein $R^4$ represents hydrogen, alkyl, aryl, substituted alkyl or substituted aryl.

8. The process of claim 1, wherein said substituted unsaturated hydrocarbon is an alkene represented by the formula:

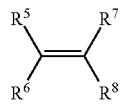

and wherein $R^5$, $R^6$, $R^7$, and $R^8$ represent hydrogen, alkyl, aryl, substituted alkyl or substituted aryl.

9. The process of claim 1, wherein said substituted unsaturated hydrocarbon is an alkyne represented by the formula:

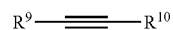

and wherein $R^9$ and $R^{19}$ represent hydrogen, alkyl, aryl, substituted alkyl or substituted aryl.

* * * * *